(12) United States Patent
Fukazawa et al.

(10) Patent No.: US 11,474,334 B2
(45) Date of Patent: Oct. 18, 2022

(54) OBSERVATION DEVICE AND OBSERVATION METHOD

(71) Applicant: SONY CORPORATION, Tokyo (JP)

(72) Inventors: Takanori Fukazawa, Kanagawa (JP); Goro Fujita, Kanagawa (JP); Koichiro Kishima, Kanagawa (JP)

(73) Assignee: SONY CORPORATION, Tokyo (JP)

(*) Notice: Subject to any disclaimer, the term of this patent is extended or adjusted under 35 U.S.C. 154(b) by 133 days.

(21) Appl. No.: 16/967,605

(22) PCT Filed: Jan. 16, 2019

(86) PCT No.: PCT/JP2019/001007
§ 371 (c)(1),
(2) Date: Aug. 5, 2020

(87) PCT Pub. No.: WO2019/159583
PCT Pub. Date: Aug. 22, 2019

(65) Prior Publication Data
US 2021/0271061 A1 Sep. 2, 2021

(30) Foreign Application Priority Data
Feb. 14, 2018 (JP) .............................. JP2018-024289

(51) Int. Cl.
*G02B 21/00* (2006.01)
*A61B 1/045* (2006.01)
(Continued)

(52) U.S. Cl.
CPC .......... *G02B 21/0052* (2013.01); *A61B 1/045* (2013.01); *A61B 1/07* (2013.01); *G02B 21/0032* (2013.01); *G02B 23/2461* (2013.01)

(58) Field of Classification Search
CPC ............ G02B 21/0052; G02B 21/0032; G02B 23/2461; G02B 5/201; G02B 21/082;
(Continued)

(56) References Cited

U.S. PATENT DOCUMENTS

2014/0350365 A1  11/2014  Sato
2015/0141753 A1*  5/2015  Kanamori ............ H04N 5/2256
                                                600/109
(Continued)

FOREIGN PATENT DOCUMENTS

CN    103987316 A    8/2014
EP      2957215 A1   12/2015
(Continued)

OTHER PUBLICATIONS

International Search Report and Written Opinion of PCT Application No. PCT/JP2019/001007, dated Apr. 16, 2019, 10 pages of ISRWO.

*Primary Examiner* — John R Schnurr
(74) *Attorney, Agent, or Firm* — Chip Law Group

(57) ABSTRACT

[Object] An observation device according to an embodiment of the present technology includes an emission unit, an imaging unit, a polarization control unit, and a calculation unit. The emission unit sequentially emits a plurality of polarization light beams of mutually different polarization directions to a biological tissue. The imaging unit includes a plurality of pixels capable of outputting pixel signals respectively. The polarization control unit considers a predetermined number of pixels of the plurality of pixels as one group and causes mutually different polarization components of reflection light beams reflected by the biological tissue to be respectively incident upon respective ones of the predetermined number of pixels included in the one group. The calculation unit calculates biological tissue information
(Continued)

regarding the biological tissue on the basis of the pixel signals output from the respective ones of the predetermined number of pixels.

18 Claims, 18 Drawing Sheets

(51) Int. Cl.
*A61B 1/07* (2006.01)
*G02B 23/24* (2006.01)

(58) Field of Classification Search
CPC .............. G02B 21/367; G02B 21/0092; G02B 23/2469; G02B 27/286; G02B 27/288; A61B 1/045; A61B 1/07; A61B 1/00006; A61B 1/00009; A61B 1/00186; A61B 1/00188; A61B 1/042; A61B 1/0661; A61B 1/0646; G01N 21/21
See application file for complete search history.

(56) References Cited

U.S. PATENT DOCUMENTS

| | | | |
|---|---|---|---|
| 2017/0295297 A1* | 10/2017 | Ishimatsu | G02B 27/286 |
| 2017/0351103 A1* | 12/2017 | Duckett | H04N 5/2258 |
| 2021/0118931 A1* | 4/2021 | Matsunuma | H01L 27/14625 |

FOREIGN PATENT DOCUMENTS

| | | |
|---|---|---|
| JP | 2013-126509 A | 6/2013 |
| JP | 2015-033587 A | 2/2015 |
| JP | 2016-063928 A | 4/2016 |
| WO | 2014/125529 A1 | 8/2014 |

* cited by examiner

OBSERVATION DEVICE AND OBSERVATION METHOD

CROSS REFERENCE TO RELATED APPLICATIONS

This application is a U.S. National Phase of International Patent Application No. PCT/JP2019/001007 filed on Jan. 16, 2019, which claims priority benefit of Japanese Patent Application No. JP 2018-024289 filed in the Japan Patent Office on Feb. 14, 2018. Each of the above-referenced applications is hereby incorporated herein by reference in its entirety.

TECHNICAL FIELD

The present technology relates to an observation device and an observation method that are applicable to biological tissue observation or the like.

BACKGROUND ART

Conventionally, technologies of observing a biological tissue irradiated with polarization light have been developed. For example, Patent Literature 1 describes a polarization image measurement display system that displays a polarization property of a site of lesion or the like. According to Patent Literature 1, an imaging section captures 16 or more light intensity polarization images in different polarization states. A polarization conversion process section calculates a Mueller matrix of 4 rows×4 columns on the basis of the light intensity polarization images, and generates a polarization property image that shows a polarization property such as a depolarization ratio of a sample or a polarization ratio of light by using the Mueller matrix. When a combination of such polarization property images is displayed, it is possible for a doctor to identify presence or absence of a collagen fiber or the like (see paragraphs [0022], [0044] to [0046], [0094], FIGS. 7 and 15 or the like of Patent Literature 1).

CITATION LIST

Patent Literature

Patent Literature 1: Japanese Patent Application Laid-open No. 2015-33587

DISCLOSURE OF INVENTION

Technical Problem

Such biological tissue observation using polarization is expected to be applied to various situations such as surgery, medical diagnosis, and the like. Technologies capable of sufficiently assisting a biological tissue in detail have been desired.

In view of the above-mentioned circumstances, it is an object of the present technology to provide an observation device and an observation method capable of sufficiently assisting biological tissue observation.

Solution to Problem

In order to accomplish the above-mentioned object, an observation device according to an embodiment of the present technology includes an emission unit, an imaging unit, a polarization control unit, and a calculation unit.

The emission unit sequentially emits a plurality of polarization light beams of mutually different polarization directions to a biological tissue.

The imaging unit includes a plurality of pixels capable of outputting pixel signals respectively.

The polarization control unit considers a predetermined number of pixels of the plurality of pixels as one group and causes mutually different polarization components of reflection light beams reflected by the biological tissue to be respectively incident upon respective ones of the predetermined number of pixels included in the one group.

The calculation unit calculates biological tissue information regarding the biological tissue on the basis of the pixel signals output from the respective ones of the predetermined number of pixels.

In this observation device, the plurality of polarization light beams different in the polarization direction is sequentially emitted to the biological tissue. The polarization states of the reflection light beams from the biological tissue are controlled and the reflection light beams from the biological tissue are incident upon the plurality of pixels, the predetermined number of pixels being considered as the one group. At this time, the mutually different polarization components are incident upon the respective ones of the predetermined number of pixels. Then, the biological tissue information regarding the biological tissue is calculated on the basis of the pixel signals output from the respective ones of the predetermined number of pixels. With this configuration, it is possible to sufficiently assist biological tissue observation.

The mutually different polarization components may be polarization components corresponding to the respective polarization directions of the plurality of polarization light beams sequentially emitted.

With this configuration, it is possible to detect the polarization components corresponding to the emitted polarization light beams for each group and it is possible to specifically observe a biological tissue, for example.

The emission unit may sequentially emit the plurality of polarization light beams such that emission periods of the plurality of polarization light beams do not overlap each other.

With this configuration, it is possible to switch the polarization directions of the polarization light beams emitted to the biological tissue at high speed. As a result, it is possible to obtain data and the like necessary for calculation of the biological tissue information at high speed.

The calculation unit may extract, from the pixel signals output from the respective ones of the plurality of pixels, the pixel signal of a pixel upon which a polarization component corresponding to a polarization direction of a polarization light beam emitted during an emission period is incident and calculates the biological tissue information on the basis of the extracted pixel signal.

With this configuration, it is possible to calculate the biological tissue information at high speed and it is possible to realize specific biological tissue observation in real time, for example. As a result, it is possible to sufficiently assist biological tissue observation.

The emission unit may sequentially emit the plurality of polarization light beams whose respective polarization directions are included in an angle range between a reference direction and an orthogonal direction orthogonal to the reference direction.

With this configuration, it is possible to realize imaging necessary for crossed nicols observation and the like at high speed, for example.

The polarization control unit may include a plurality of polarization elements, the plurality of polarization elements being arranged corresponding to the predetermined number of pixels in each group and each having a polarization axis corresponding to each of the respective polarization directions of the plurality of polarization light beams.

With this configuration, it is possible to easily control the polarization states of the polarization components that are incident upon the respective ones of the predetermined number of pixels. As a result, it is possible to accurately observe the biological tissue.

The plurality of polarization elements may each have the polarization axis that intersects with a polarization direction of a corresponding polarization light beam of the plurality of polarization light beams at a predetermined angle of intersection.

With this configuration, it is possible to control the polarization directions of the polarization components incident upon the respective ones of the predetermined number of pixels with high accuracy. As a result, it is possible to enhance the accuracy of biological tissue observation.

The predetermined angle of intersection may be 90°±2°.

With this configuration, it is possible to observe the biological tissue in a substantially crossed nicols state. As a result, a change in the polarization direction or the like due to the biological tissue is detected with high accuracy, and it is possible to sufficiently assist biological tissue observation.

The imaging unit may include an image sensor including the plurality of pixels. In this case, the predetermined number of pixels may be a pixel group including four pixels provided in the image sensor with two of the four pixels arranged in each of two directions orthogonal to each other. Moreover, the plurality of polarization elements may be a polarization element group including four or less polarization elements arranged corresponding to the pixel group.

With this configuration, it is possible to arrange the polarization elements in accordance with the color filter or the like and it is possible to easily realize biological tissue color observation using polarization light or the like, for example.

The polarization element group may include a polarization element having a polarization axis rotated by about 90° in a predetermined direction from a reference direction, a polarization element having a polarization axis rotated by about 112.5 v in the predetermined direction from the reference direction, a polarization element having a polarization axis rotated by about 135° in the predetermined direction from the reference direction, and a polarization element having a polarization axis rotated by about 157.5° in the predetermined direction from the reference direction.

With this configuration, for example, it is possible to realize substantially crossed nicols observation with respect to the biological tissue appropriately and it is possible to sufficiently assist biological tissue observation.

The polarization element group may include a polarization element having a polarization axis rotated by about 90° in a predetermined direction from a reference direction, a polarization element having a polarization axis rotated by about 120° in the predetermined direction from the reference direction, and a polarization element having a polarization axis rotated by about 150° in the predetermined direction from the reference direction.

With this configuration, it is possible to constitute the pixels in which the filter and the like other than the polarization elements are provided and specific biological tissue observation is possible, for example.

The emission unit may include a plurality of light sources and a plurality of polarization sections that respectively generates plurality of polarization light beams of the mutually different polarization directions from respective emission light beams of the plurality of light sources.

With this configuration, it is possible to switch the plurality of polarization light beams at high speed and emit them, for example. As a result, it is possible to realize specific biological tissue observation in real time.

The emission unit may include a light source and a polarization section capable of rotating a polarization direction of a polarization light beam generated from an emission light beam of the light source.

With this configuration, it is possible to emit the plurality of polarization light beams by using the single light source and the polarization section and it is possible to configure the device to be compact.

The imaging unit may include a first image sensor including a plurality of first pixels and a second image sensor including a plurality of second pixels. In this case, the observation device may further include: a separation optical system that separates a reflection light beam from the biological tissue into a first separated light beam and a second separated light beam that travel in mutually different directions, causes the first separated light beam to be incident upon the first image sensor, and causes the second separated light beam to be incident upon the second image sensor.

As described above, it is possible to specifically observe a biological tissue, for example, by performing observation using the two image sensors.

The polarization control unit may include a plurality of first polarization elements that is arranged corresponding to the predetermined number of the first pixels, the predetermined number of the first pixels being considered as a first group, and a plurality of second polarization elements that is arranged corresponding to the predetermined number of the second pixels, the predetermined number of the second pixels being considered as a second group.

With this configuration, it is possible to detect the polarization components of the respective reflection light beams through the two image sensors and it is possible to sufficiently specifically observe the biological tissue.

The emission unit may be capable of emitting a non-polarization light beam to the biological tissue. In this case, the calculation unit may obtain a plurality of pixel signals output from the first pixels and the second pixels included in the first group and the second group in a case where the non-polarization light beam is emitted.

With this configuration, it is possible to realize observation of the open nicol state in addition to observation of the substantially crossed nicols state, for example. As a result, it is possible to sufficiently specifically observe the biological tissue.

The plurality of first polarization elements may include a polarization element having a polarization axis substantially parallel to a reference direction, a polarization element having a polarization axis rotated by about 45° in the predetermined direction from the reference direction, a polarization element having a polarization axis rotated by about 90° in the predetermined direction from the reference direction, and a polarization element having a polarization axis rotated by about 135° in the predetermined direction from the reference direction. In this case, the plurality of second polarization elements may include a polarization element having a polarization axis rotated by about 22.5° in the predetermined direction from the reference direction, a polarization element having a polarization axis rotated by about 67.5° in the predetermined direction from the reference direction, a polarization element having a polarization axis rotated by about 112.5° in the predetermined direction from the reference direction, and a polarization element having a polarization axis rotated by about 157.5° in the predetermined direction from the reference direction.

With this configuration, it is possible to use the polarization camera or the like having polarization axes with a pitch of 45° and it is possible to easily constitute the observation device.

The second image sensor may be capable of detecting the second separated light beam while maintaining a polarization state of the second separated light beam.

With this configuration, it is possible to monitor the biological tissue with high resolution, for example.

The observation device may be configured as an endoscope or a microscope.

It is possible to sufficiently assist biological tissue observation in inspection or the like using the endoscope or the microscope.

An observation method according to an embodiment of the present technology is an observation method to be performed by a computer system and includes sequentially emitting a plurality of polarization light beams of mutually different polarization directions to a biological tissue.

For each group including a predetermined number of pixels of a plurality of pixels, pixel signals output from the respective ones of the predetermined number of pixels upon which mutually different polarization components of reflection light beams reflected by the biological tissue, are respectively incident are obtained.

Biological tissue information regarding the biological tissue is calculated on the basis of the obtained pixel signals.

Advantageous Effects of Invention

As described above, in accordance with the present technology, it is possible to sufficiently assist biological tissue observation. It should be noted that the effects described here are not necessarily limitative and any effect described in the present disclosure may be provided.

MODE(S) FOR CARRYING OUT THE INVENTION

Hereinafter, embodiments according to the present technology will be described with reference to the drawings.

First Embodiment

[Configuration of Observation Apparatus]

Figure 1:
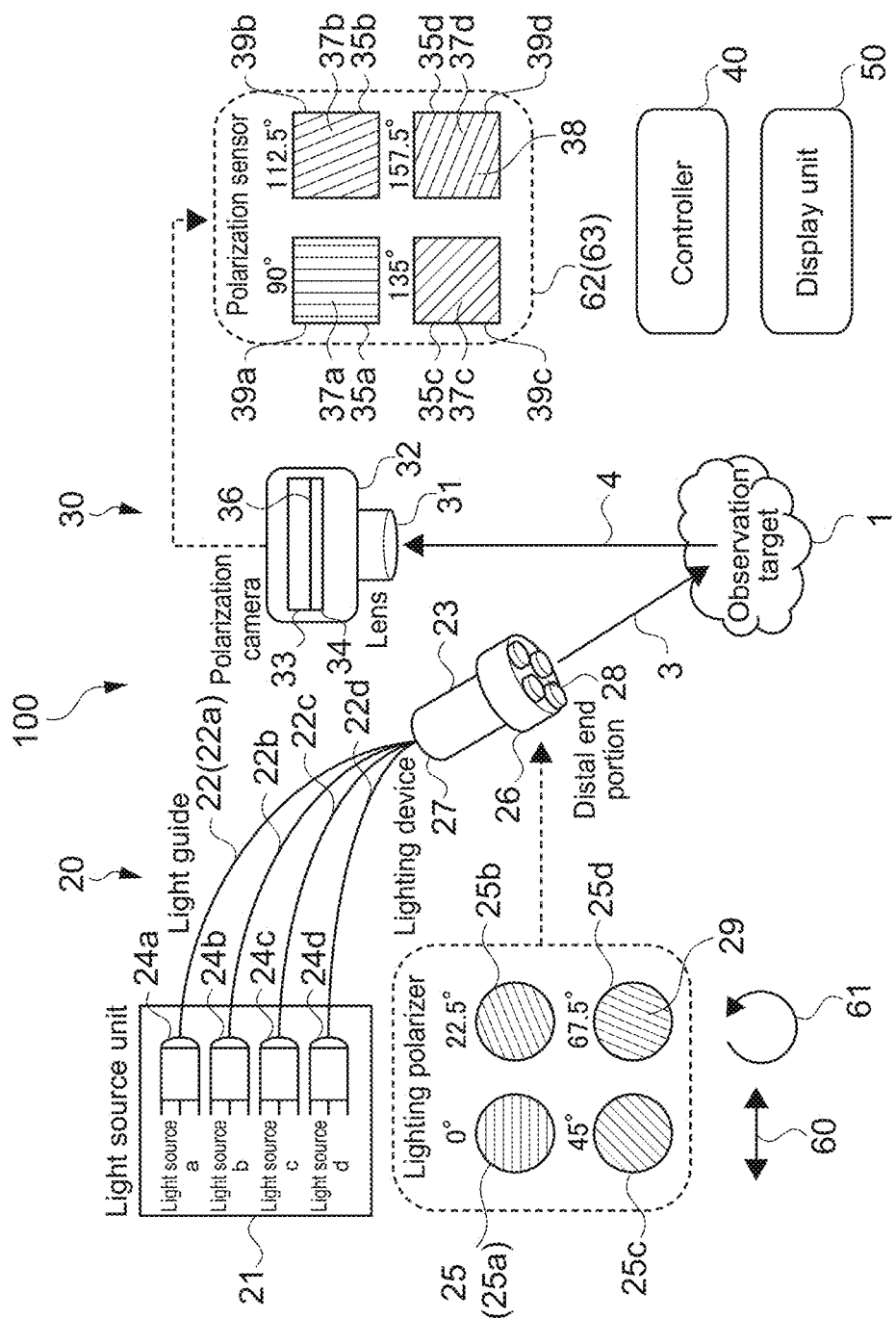
FIG. 1 A schematic view showing a configuration example of a microscope device that is an observation device according to a first embodiment of the present technology.

FIG. 1 is a schematic view showing a configuration example of a microscope device 100 that is an observation device according to a first embodiment of the present technology. The microscope device 100 includes a lighting system 20, an imaging system 30, a controller 40, and a display unit 50.

The microscope device 100 is used for observing a site or the like that is an observation target 1 during surgery such as laparotomy and incision surgery, for example. It should be noted that not limited to a case where the microscope device 100 is used during surgery, the microscope device 100 may be used when observing a lesion sample or the like, for example. In this embodiment, a biological tissue is the observation target 1.

The lighting system 20 includes a light source unit 21, a light guide 22, and a lighting device 23. The light source unit 21 includes a plurality of light sources 24. In this embodiment, four light sources 24a to 24d are used as the plurality of light sources 24. Moreover, a non-polarization light beam is emitted from each of the light sources 24a to 24d as an emission light beam. A white light emitting diode (LED), a xenon lamp, or the like is used as each of the light sources 24. In addition to this, an arbitrary light source 24 capable of emitting the non-polarization light beam may be used as appropriate.

The light guide 22 transmits the emission light beams emitted from the plurality of light sources 24 of the light source unit 21. The light guide 22 includes light guides 22a to 22d connected to the light sources 24a to 24d respectively. Therefore, emission light beams output from the respective light sources 24 are individually transmitted through the respective different light guides 22. An optical fiber such as a single fiber and bundled fibers, for example, is used as the light guide 22.

The lighting device 23 includes a plurality of polarizers 25. The lighting device 23 has a tubular shape and includes a distal end portion 26 and a rear end portion 27 opposite to the distal end portion 26. As shown in FIG. 1, the plurality of polarizers 25 are arranged at the distal end portion 26. Moreover, the light guide 22 is connected to the rear end portion 27. The lighting device 23 is arranged with the distal end portion 26 (the plurality of polarizers 25) directed to the observation target 1. Moreover, the lighting device 23 is retained by a retaining mechanism (not shown) such that the position, the attitude, and the like can be adjusted.

The plurality of polarizers 25 is respectively arranged on a setting surface 28 provided at the distal end portion 26 of the lighting device 23. That is, the plurality of polarizers 25 are respectively arranged on an identical plane (the setting surface 28). Emission light beams from the plurality of light sources 24 are respectively incident upon the plurality of polarizers 25. For example, the lighting device 23 is configured as appropriate such that the emission light beams from the plurality of light sources 24 which have been transmitted by the light guide 22 are incident upon the plurality of polarizers 25 respectively.

In addition, the plurality of polarizers 25 respectively generate a plurality of polarization light beams of mutually different polarization directions from the emission light beams of the plurality of light sources 24. For example, the polarizer 25 generates a polarization light beam (straight polarization light beam) of a polarization direction parallel to its polarization axis 29 from the emission light beam that has been incident upon the polarizer 25. Therefore, each of the mutually different polarization axes 29 is set to each of the plurality of polarizers 25.

A specific configuration of the polarizer 25 is not limited, and the polarizer 25 using a wire grid, a liquid-crystal device, a polarization film, and the like may be used as appropriate. Hereinafter, the polarizer 25 provided in the lighting device 23 will be described as a lighting polarizer 25 with the same reference sign. In this embodiment, the lighting polarizer 25 corresponds to a polarization section.

FIG. 1 schematically shows an arrangement example of the lighting polarizer 25 as the lighting device 23 is viewed from the side of the observation target 1. In this embodiment, four lighting polarizers 25a to 25d are used. Emission light beams of the four light sources 24a to 24d are respectively incident upon the respective lighting polarizers 25a to 25d. As shown in FIG. 1, the lighting polarizers 25a to 25d are configured such that the respective polarization axes 29 are in mutually different directions. The direction of the polarization axis 29 is, for example, a direction in which the polarization axis 29 extends and is a direction parallel to the setting surface 28.

The respective polarization axes 29 of the respective lighting polarizers 25a to 25d can be expressed by using a reference direction 60 that becomes a reference for indicating the direction of the polarization axis 29, a direction of rotation 61 from the reference direction 60, and a rotational angle. In this embodiment, the direction parallel to the polarization axis 29 of the lighting polarizer 25a is set as the reference direction 60. Moreover, as the lighting device 23 is viewed from the side of the distal end portion 26, a direction of rotating in a direction of left rotation (counterclockwise) in the surface of the setting surface 28 is set as the direction of rotation 61. For example, in FIG. 1, left and right directions in the figure are the reference direction 60 and a direction of rotating in the direction of left rotation on the sheet is the direction of rotation 61.

In this embodiment, each of the mutually different polarization axes 29 included in an angle range between the reference direction 60 and an orthogonal direction orthogonal to the reference direction 60 is set to each of the plurality of lighting polarizers 25. That is, each polarization axis 29 is set such that the rotational angle in the direction of left rotation from the reference direction 60 is 0° or more and 90° or less (or less than 90°).

As shown in FIG. 1, the lighting polarizer 25a has the polarization axis 29 parallel to the reference direction 60. That is, it can also be said that the lighting polarizer 25a has the polarization axis 29 rotated by 0° in the direction of left rotation from the reference direction 60. The lighting polarizer 25b has the polarization axis 29 rotated by about 22.5° in the direction of left rotation from the reference direction 60. The lighting polarizer 25c has the polarization axis 29 rotated by about 45° in the direction of left rotation from the reference direction 60. The lighting polarizer 25d has the polarization axis 29 rotated by about 67.5° in the direction of left rotation from the reference direction 60.

It should be noted that in the present disclosure, the recitation "about 22.5°", "about 45°", and "about 67.5°" include 22.5°, 45°, and 67.5° respectively. The same applies to other recitation related to the angles.

Therefore, it can also be said that the polarization axes 29 of the lighting polarizers 25a to 25d are set by using an angle (90°/4=22.5°) obtained by dividing the angle range of from the reference direction 60 to the orthogonal direction into four parts in the direction of left rotation as a reference. That is, a rotational angle θ in the direction of left rotation of each polarization axis 29 is expressed as θ=22.5×(n−1). Here, n indicates an integer and the lighting polarizers 25a to 25d correspond to n=1 to 4.

As described above, in the lighting system 20, emission light beams from the plurality of light sources 24a to 24d is respectively incident upon the plurality of lighting polarizers 25a to 25d via the light guide 22. Then, the plurality of lighting polarizers 25a to 25d emits polarization light beams 3 of polarization directions whose rotational angles θ with respect to the reference direction 60 are 0°, about 22.5°, about 45°, and about 67.5° toward the observation target 1. Hereinafter, the rotational angle θ of each polarization light beam 3 will be referred to as an incident polarization angle θ and the polarization axis 29 of the lighting polarizer 25 will be referred to as an incident polarization axis 29 in some cases. Moreover, the word "about" will be omitted from recitation related to the incident polarization angle θ in some cases.

It should be noted that the plurality of light sources 24a to 24d is controlled to sequentially emit emission light beams. Therefore, the polarization light beams 3 whose incident polarization angles θ are 0°, 22.5°, 45°, and 67.5° are emitted in order from the plurality of lighting polarizers 25a to 25d. As described above, the lighting system 20 sequentially emits the plurality of polarization light beams of the mutually different polarization directions to the observation target 1. FIG. 1 schematically shows one of the polarization light beams 3 emitted from the lighting system 20 by using the arrow. A method of emitting the emission light beams and the like will be described later in detail. In this embodiment, the lighting system 20 corresponds to an emission unit.

The imaging system 30 includes a lens unit 31 and a polarization camera 32. As shown in FIG. 1, in the imaging system 30, the lens unit 31 and the polarization camera 32 are integrally configured and the imaging system 30 is arranged with the lens unit 31 directed to the observation target 1. Moreover, the imaging system 30 is retained by a retaining mechanism (not shown) such that the position and the attitude can be adjusted.

The lens unit 31 is constituted by one or more lenses (not shown), for example. A reflection light beam 4 when an illumination light beam (the polarization light beam 3) of the lighting system 20 is reflected by the observation target 1 is incident upon the lens unit 31. FIG. 1 schematically shows the reflection light beam 4 reflected by the observation target 1 by using the arrow.

The lens unit 31 has an optical zoom function and the like and generates, for example, an optical image of the observation target 1 which has been optically enlarged or reduced by controlling imaging parameters such as the f-number (diaphragm value) and optical magnification. A specific configuration for realizing the optical zoom function is not limited, and it may be possible to perform automatic zoom, manual zoom, or the like by electronic control as appropriate, for example.

The polarization camera 32 includes an image sensor 33 and a polarization unit 34. Moreover, the polarization camera 32 includes a color filter (not shown).

The image sensor 33 includes a plurality of pixels 35 capable of outputting pixel signals respectively. The plurality of pixels 35 is arrayed in two directions orthogonal to each other on the light-receiving surface 36 of the image sensor 33 (see FIG. 2). In the image sensor 33, the intensity of an incident light beam incident upon each pixel 35 is detected and the detection result is output as a pixel signal.

For example, a polarizer 37 and a color filter to be described later are arranged on the side of the light-receiving surface 36 of the pixel 35. A signal indicating the intensity of a light beam that has passed through the polarizer 37 and the color filter is the pixel signal. It should be noted that FIG. 1 schematically shows the four pixels 35a to 35d in which the polarizers 37 (the polarization unit 34) are arranged.

In the light-receiving surface 36 of the image sensor 33, an optical image of the observation target 1 is formed by the above-mentioned lens unit 31. Then, the intensity (brightness) of an optical image at the position of each pixel 35 is detected as the pixel signal. With this configuration, it is possible to realize image observation of the observation target 1 or the like.

A specific configuration of the image sensor 33 is not limited, and a complementary metal-oxide semiconductor (CMOS) sensor, a charge coupled device (CCD) sensor, or the like may be used as appropriate, for example. In this embodiment, the image sensor 33 functions as an imaging unit.

The polarization unit 34 includes the plurality of polarizers 37 arranged on the side of the light-receiving surface 36 of the image sensor 33. The polarizers 37 each have a size substantially equal to the size of each of the plurality of pixels 35 of the image sensor 33 and are arranged corresponding to the plurality of pixels 35 of the image sensor 33. That is, the polarization unit 34 is configured such that the single polarizer 37 is arranged on the side of the light-receiving surface 36 of the single pixel 35. Therefore, the number of polarizers 37 is equal to the number of pixels 35.

Respective polarization axes 38 are set to the plurality of polarizers 37. For example, when a light beam is incident upon a certain polarizer 37, a polarization component (straight polarization light beam) of a polarization direction parallel to the polarization axis 38 of the polarizer 37 is extracted.

As shown in FIG. 1, in the polarization camera 32, the reflection light beam 4 reflected by the observation target 1 is incident upon the polarization unit 34 (the plurality of polarizers 37) via the lens unit 31. The plurality of polarizers 37 extracts polarization components parallel to the respective polarization axes 38 from the reflection light beams 4 that have been incident thereon and causes the extracted polarization components to be incident upon the corresponding pixels 35. That is, it can also be said that the plurality of polarizers 37 controls the polarization directions of the reflection light beams 4 that travel toward the corresponding pixels 35.

The plurality of polarizers 37 is formed on the side of the light-receiving surface 36 of the respective pixels 35 in accordance with a process of generating the plurality of pixels 35 of the image sensor 33, for example. That is, the polarization unit 34 is constituted by the plurality of polarizers 37 formed on the plurality of pixels 35. A specific configuration of the polarizer 37 is not limited, and the polarizer 37 using a wire grid, a liquid-crystal device, a polarization film, and the like may be used as appropriate.

Hereinafter, the polarizer 37 arranged corresponding to the pixel 35 of the image sensor 33 will be referred to as a light-receiving polarizer 37 with the same reference sign. Moreover, the polarization axis 38 of the light-receiving polarizer 37 will be referred to as a polarization transmission axis 38. In this embodiment, the polarization unit 34 corresponds to a polarization control unit and the light-receiving polarizer 37c corresponds to a polarization element.

The polarization unit 34 considers a predetermined number of pixels 35 of the plurality of pixels 35 as one group and causes the mutually different polarization components of the reflection light beams 4 reflected by the observation target 1 to be respectively incident upon the predetermined number of pixels 35 included in the one group. Specifically, the mutually different polarization transmission axes 38 are set to a predetermined number of light-receiving polarizers 37 arranged in the predetermined number of pixels 35 of the group. In the polarization camera 32, a plurality of such groups of the predetermined number of pixels 35 and the predetermined number of light-receiving polarizers 37 is set.

FIG. 1 schematically shows a configuration example of the group including the predetermined number of pixels 35 and the predetermined number of light-receiving polarizers 37. As shown in FIG. 1, in this embodiment, a pixel group 62 is selected as the predetermined number of pixels 35, the pixel group 62 including the four pixels 35a to 35d provided in the image sensor 33 with two of the four pixels 35a to 35d arranged in each of the two directions orthogonal to each other. Moreover, a polarizer group 63 is used as the predetermined number of light-receiving polarizers 37, the polarizer group 63 including four light-receiving polarizers 37a to 37d arranged corresponding to the pixel group 62. In this embodiment, the polarizer group 63 corresponds to a polarization element group.

The polarization transmission axes 38 of the four light-receiving polarizers 37a to 37d are set to correspond to the above-mentioned incident polarization axes 29 of the plurality of lighting polarizers 25a to 25d. Therefore, the mutually different polarization components that are incident upon the respective pixels 35a to 35d included in the one group are the polarization components corresponding to the respective polarization directions of the plurality of polarization light beams 3 sequentially emitted from the lighting system 20.

As described above, the polarization unit 34 includes the plurality of light-receiving polarizers 37 (the light-receiving polarizers 37a to 37d) having the polarization transmission axes 38 respectively corresponding to the respective polarization directions of the plurality of polarization light beams 3, the plurality of light-receiving polarizers 37 being arranged corresponding to the predetermined number of pixels 35 (the pixels 35a to 35d) for each group.

Moreover, the plurality of light-receiving polarizers 37 each have the polarization transmission axis 38 that intersects with the polarization direction of the corresponding polarization light beam of the plurality of polarization light beams 3 at a predetermined angle of intersection.

The predetermined angle of intersection is set to be 90°±2°. Influences of the reflection light beams 4 reflected in the vicinity of the surface of the observation target 1 to be described later can be sufficiently avoided by setting the polarization transmission axis 38 within the range of this angle of intersection. With this configuration, a biological tissue can be observed with high accuracy.

It should be noted that the range of the predetermined angle of intersection is not limited and may be set as appropriate as long as allowed observation accuracy can be provided. For example, an angle within a range wider than 90°±2°, for example, 90°±5° or 90°±10° may be set as an angle of intersection Φ. The predetermined angle of intersection may be set as appropriate in a manner that depends on the type of observation target 1 or the characteristics of the lighting system 20 and the imaging system 30, for example.

In this embodiment, the predetermined angle of intersection is set to be about 90°. Therefore, the plurality of light-receiving polarizers 37 includes the light-receiving polarizer 37 having the polarization transmission axis 38 that intersects with the incident polarization angle θ of each polarization light beam 3 emitted from the lighting system 20 at about 90°.

In the example shown in FIG. 1, the light-receiving polarizer 37a having the polarization transmission axis 38 rotated by about 90° in the direction of left rotation from the reference direction 60 is arranged at the upper left of the polarizer group 63. Therefore, the polarization transmission axis 38 of the light-receiving polarizer 37a intersects with the polarization direction (the reference direction 60) of the polarization light beam 3 emitted from the lighting polarizer 25a at about 90°. In this case, the polarization light beam 3 emitted from the lighting polarizer 25a is the corresponding polarization light beam of the light-receiving polarizer 37a.

The light-receiving polarizer 37b having the polarization transmission axis 38 rotated by about 112.5° in the direction of left rotation from the reference direction 60 is arranged at the upper right of the polarizer group 63. Therefore, the polarization transmission axis 38 of the light-receiving polarizer 37b intersects with the polarization direction of the polarization light beam 3 emitted from the lighting polarizer 25b (the direction rotated by about 22.5° in the direction of left rotation from the reference direction 60) at about 90°. In this case, the polarization light beam 3 emitted from the lighting polarizer 25a is the corresponding polarization light beam of the light-receiving polarizer 37a.

The light-receiving polarizer 37c having the polarization transmission axis 38 rotated by about 135° in the direction of left rotation from the reference direction 60 is arranged at the lower left of the polarizer group 63. Therefore, the polarization transmission axis 38 of the light-receiving polarizer 37c intersects with the polarization direction of the polarization light beam 3 emitted from the lighting polarizer 25c (the direction rotated by about 45° in the direction of left rotation from the reference direction 60) at about 90°. In this case, the polarization light beam 3 emitted from the lighting polarizer 25c is the corresponding polarization light beam of the light-receiving polarizer 37c.

The light-receiving polarizer 37d having the polarization transmission axis 38 rotated by about 157.5° in the direction of left rotation from the reference direction 60 is arranged at the lower right of the polarizer group 63. Therefore, the polarization transmission axis 38 of the light-receiving polarizer 37d intersects with the polarization direction of the polarization light beam 3 emitted from the lighting polarizer 25d (the direction rotated by about 67.5° in the direction of left rotation from the reference direction 60) at about 90°. In this case, the polarization light beam 3 emitted from the lighting polarizer 25d is the corresponding polarization light beam of the light-receiving polarizer 37d.

It should be noted that the reference direction 60 in the polarization camera 32 is the polarization direction of the reflection light beam 4 in a case where the polarization light beam 3 emitted from the lighting polarizer 25a is reflected without changing its polarization direction, for example. For example, in a case where specular reflection or the like occurs at the observation target 1, the polarization light beam 3 is reflected without changing the polarization direction (the incident polarization angle θ). The polarization direction of the reflection light beam 4 in this case is the reference direction 60.

The rotational angle of the polarization transmission axis 38 is not limited and can be set as appropriate as long as allowed observation accuracy can be provided. It should be noted that in the present disclosure, the wordings "about 90°", "about 112.5°", "about 135°", and "about 157.5°" include 90°, 112.5°, 135°, and 157.5° respectively. The same applies to other recitation related to the angles.

The arrangement relationship between the polarization transmission axes 38 can be adjusted by, for example, rotating the lighting device 23 using the emission direction of the polarization light beam 3 as an axis or rotating the polarization camera 32 using the incident direction of the reflection light beam 4 (a lens optical axis) as an axis. That is, the lighting device 23 or the polarization camera 32 is rotated as appropriate such that the incident polarization axes 29 of the respective lighting polarizers 25a to 25d and the polarization transmission axes 38 of the respective light-receiving polarizers 37*a* to 37*d* intersect with each other at about 90°.

Hereinafter, the rotational angle of the polarization transmission axis 38 with respect to the reference direction 60 in the direction of left rotation will be referred to as a transmission angle φ in some cases. For example, the transmission angles φ of the light-receiving polarizers 37*a* to 37*d* are respectively about 90°, about 112.5°, about 135°, and about 157.5°. Hereinafter, the word "about" will be omitted from recitation related to the transmission angle φ in some cases.

It should be noted that the pixels 35 in which the light-receiving polarizers 37 are arranged function as polarization sensors that detect the polarization components having the transmission angles φ set to the light-receiving polarizers 37. Therefore, it can also be said that the polarization camera 32 functions as a polarization image sensor including four types of polarization sensors.

Hereinafter, a pair including the light-receiving polarizer 37*a* having a transmission angle of 90° will be referred to as a polarization sensor 39*a*, a pair including the light-receiving polarizer 37*b* having a transmission angle of 112.5° will be referred to as a polarization sensor 39*b*, a pair including the light-receiving polarizer 37*c* having a transmission angle of 135° will be referred to as a polarization sensor 39*c*, and a pair including the light-receiving polarizer 37*d* having a transmission angle of 157.5° will be referred to as a polarization sensor 39*d* in some cases.

Figure 2:
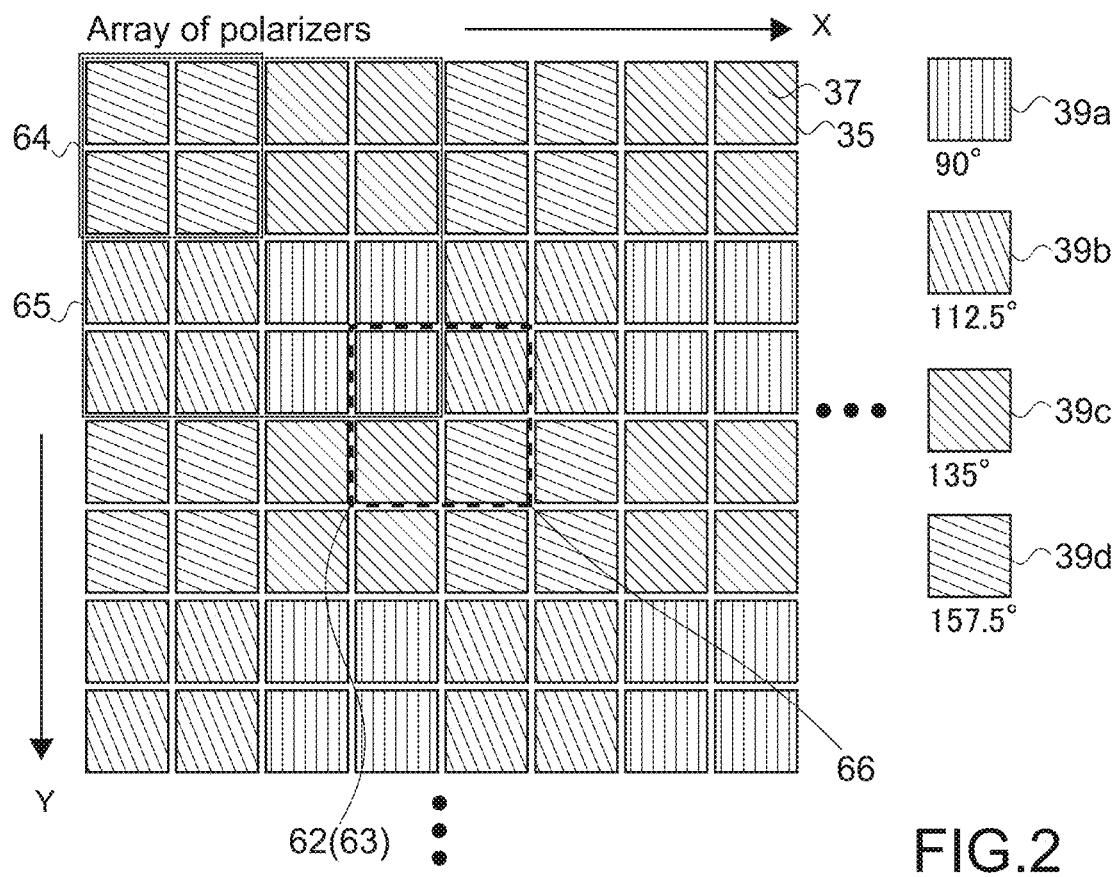
FIG. 2 A schematic view showing an example of an array of light-receiving polarizers.

FIG. 2 is a schematic view showing an example of an array of the light-receiving polarizers 37. FIG. 2 schematically shows the light-receiving polarizers 37 arranged corresponding to the plurality of pixels 35. Hereinafter, the position of the light-receiving polarizer 37 (the pixel 35) is expressed as (m, n). Where m and n are integers indicate positions in the upper and lower directions (the Y-axis) and the left and right directions (the X-axis) in the figure. Moreover, the position of the light-receiving polarizer 37 (the pixel 35) at the upper left in the figure is expressed as (1, 1).

As shown in FIG. 2, in the polarization unit 34, four types of polarization transmission axes 38 are set in units of 4×4 large blocks 65. In each large block 65, 2×2 small blocks 64 are arranged with two of them arranged in the upper and lower directions and two of them arranged in the left and right directions. For example, the four types of polarization transmission axes 38 are respectively allocated in the respective small blocks 64 included in the large block 65.

For example, in the array shown in FIG. 2, the small blocks 64 including the light-receiving polarizer 37 (1, 1) are set to have the transmission angle 157.5°. The small blocks 64 including the light-receiving polarizer 37 (1, 3) are set to have the transmission angle 135°. The small blocks 64 including the light-receiving polarizer 37 (3, 1) are set to have the transmission angle 112.5°. The small blocks 64 including the light-receiving polarizer 37 (3, 3) are set to have the transmission angle 90°.

An array pattern obtained by repeatedly arranging the 4×4 large blocks 65 in which the four types of polarization transmission axes 38 (the transmission angles φ) are set as described above in the upper and lower directions and the left and right directions is used. Moreover, as shown in FIG. 2, in this array pattern, it is possible to select a 2×2 pixel group 62 as appropriate such that the 2×2 pixel group 62 includes the four types of polarization transmission axes 38. For example, the 2×2 pixel group 62 including the light-receiving polarizer 37 (4, 4) at the upper left, which is surrounded with the dotted line in the figure, is an array similar to the pixel group 62 (the polarizer group 63) described in FIG. 1.

Hereinafter, the 2×2 pixel group 62 including the four types of polarization transmission axes 38 will be referred to as a sensor group 66 in some cases. It should be noted that in the array pattern shown in FIG. 2, four types of sensor groups 66 mutually different in arrangement of the four types of polarization transmission axes 38 exist. Such a configuration in which the arrangement is different in the sensor group 66 can also be used.

Figure 3:
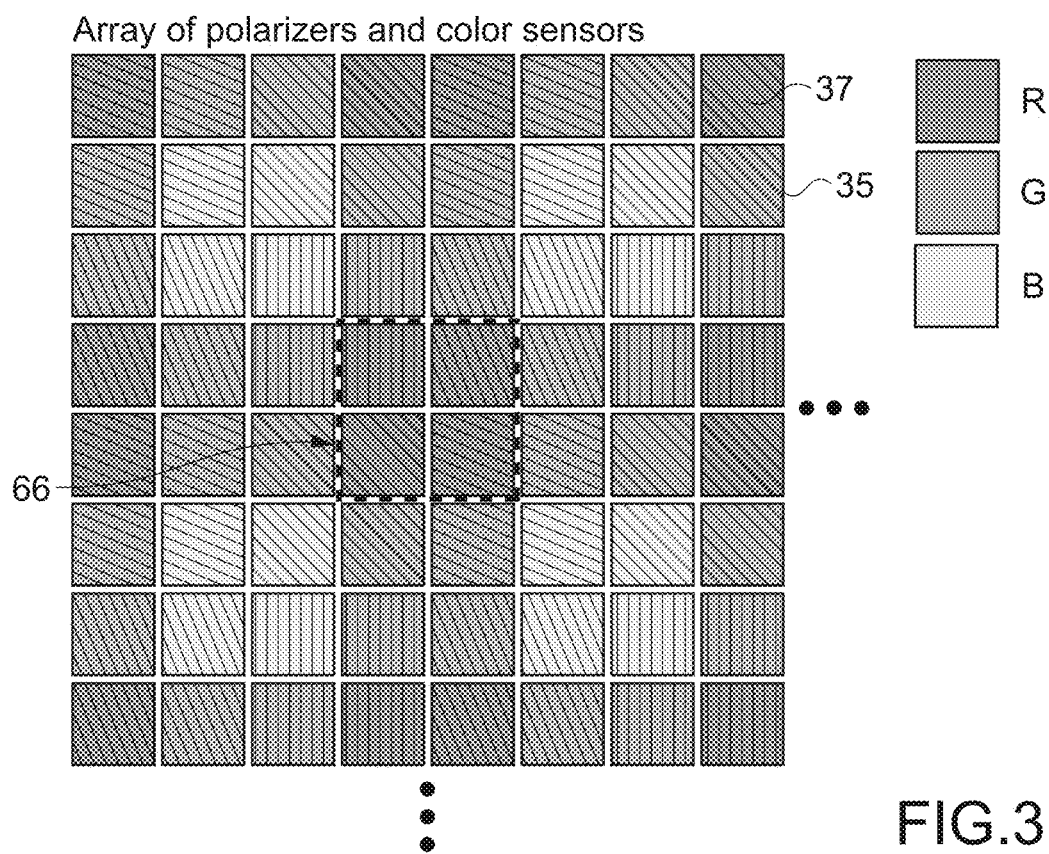
FIG. 3 A schematic view showing an example of arrays of light-receiving polarizers and color filters.

FIG. 3 is a schematic view showing an example of an array of the light-receiving polarizers 37 and the color filters. FIG. 3 shows an example of the array in a case where the color filters are arranged in the pattern of the array of the light-receiving polarizers 37 shown in FIG. 2. Three types of color filters corresponding to red (R), green (G), and blue (B), for example, are used as the color filter. It should be noted that the respective colors of red, green, and blue are expressed as dark grey, middle grey, and pale grey.

The color filters are arranged between the image sensor 33 and the polarization unit 34, i.e., between the light-receiving surfaces 36 of the pixels 35 and the light-receiving polarizers 37, for example. Alternatively, the color filters may be arranged on a side opposite to the image sensor 33 with the polarization unit 34 interposed therebetween, i.e., a side of the polarization unit 34 upon which the reflection light beam 4 is incident.

In the example shown in FIG. 3, one color (color filter) is set to one sensor group 66. That is, the four types of light-receiving polarizers 37 are arranged in the adjacent pixels 35 in the same color. With this configuration, it is possible to detect the intensity (pixel signals) of the polarization components polarized at the transmission angles φ mutually different from the adjacent pixels 35 in the same color.

In addition, the color array of the color filters is set to be the Bayer array in each sensor group 66. For example, regarding the sensor group 66 including the light-receiving polarizer 37 (4, 4), the red is set to all the pixels 35 in the sensor group 66. Moreover, the green is set to the sensor group 66 (e.g., the sensor group 66 including the light-receiving polarizer 37 (4, 6)) arranged at the upper and lower left and right of the sensor group 66 in which the red is set. Moreover, the blue is set to the sensor group 66 (e.g., the sensor group 66 including the light-receiving polarizer 37 (6, 6)) arranged at the upper right, lower right, upper left, and lower left of the sensor group 66 in which the red is set.

By using the array pattern of the polarization transmission axes 38 shown in FIGS. 2 and 3 in this manner, it is possible to realize arrangement of the color filters using the Bayer array. By arranging the light-receiving polarizers 37 and the color filters in this manner, it is possible to easily realize the polarization camera 32 capable of proper color observation and the like of the observation target 1.

The controller 40 includes hardware that is necessary for configuring a computer such as a CPU, ROM, RAM, and an HDD. An observation method according to the present technology is performed when the CPU loads a program into the RAM and executes the program according to the present technology. The program according to the present technology is recorded in the ROM or the like in advance. For example, the controller 40 can be implemented by any computer such as a personal computer (PC).

Figure 4:
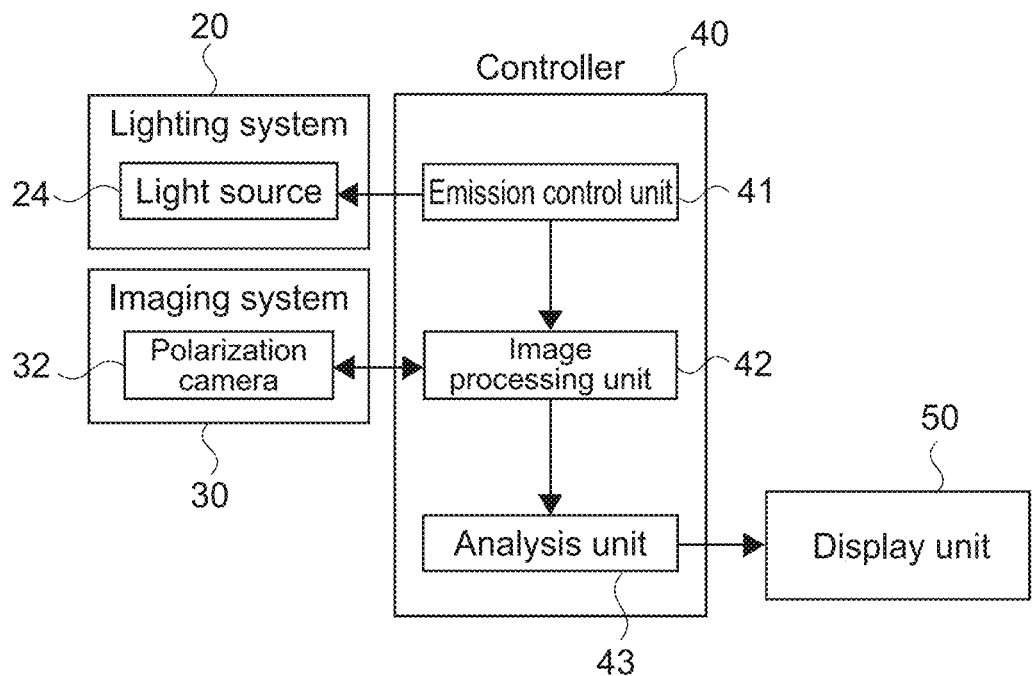
FIG. 4 A block diagram showing a configuration example of a controller.

FIG. 4 is a block diagram showing a configuration example of the controller 40. As shown in FIG. 4, in this embodiment, an emission control unit 41, an image processing unit 42, and an analysis unit 43 are configured as functional blocks when the CPU executes a predetermined program. As a matter of course, it is also possible to use dedicated hardware such as an integrated circuit (IC) to implement each of the blocks. The program is installed in the controller 40 via various kinds of recording media, for example. Alternatively, it is also possible to install the program via the Internet.

The emission control unit 41 controls operations of the plurality of light sources 24a to 24d of the lighting system 20. Specifically, with respect to the plurality of light sources 24a to 24d, timings at which an emission light beam is emitted and periods in which the emission light beam is emitted are controlled. Therefore, the emission control unit 41 is capable of controlling the emission timings and the emission periods of the plurality of polarization light beams 3 emitted from the lighting system 20. For example, the emission control unit 41 outputs, to the plurality of light sources 24a to 24d as appropriate, a start signal for starting emission of the emission light beam and a stop signal for starting emission of the emission light beam.

In this embodiment, the emission control unit 41 causes the plurality of light sources 24a to 24d to sequentially operate such that the emission periods of the plurality of light sources 24a to 24d do not overlap each other. Therefore, the lighting system 20 sequentially emits the plurality of polarization light beams 3 such that their emission periods do not overlap each other. Moreover, the emission control unit 41 generates synchronization signals according to the emission periods and the emission timings and outputs the synchronization signals to the image processing unit 42. The emission periods and the emission timings of the plurality of polarization light beams 3 (the plurality of light sources 24a to 24d) will be described later in detail.

The image processing unit 42 obtains output data from the image sensor 33 of the imaging system 30. The output data from the image sensor 33 includes pixel signals respectively output from the plurality of pixels 35 of the image sensor 33. Therefore, the image processing unit 42 reads pixel signals output from all the pixels 35 of the image sensor 33 irrespective of the directions and the like of the polarization transmission axes 38 of the light-receiving polarizers 37.

In addition, the image processing unit 42 extracts, from the pixel signals output from the respective ones of the plurality of pixels 35 obtained as the output data, a pixel signal of the pixel 35 upon which the polarization component corresponding to the polarization direction of the polarization light beam 3 emitted during the emission period is incident. The process of extracting the pixel signal is performed on the basis of the synchronization signal from the emission control unit 41, for example.

In this embodiment, when a polarization light beam 3 having a certain incident polarization angle θ is emitted, a pixel signal of the pixel 35 upon which a polarization component that intersects with the incident polarization angle θ at about 90°, i.e., a polarization component orthogonal to the polarization light beam 3 incident upon the observation target 1 is incident is extracted. Therefore, for example, (W/2)×(H/2) pixel signals are extracted by the image sensor 33 whose total number of pixels is W×H. It should be noted that W and H denote the number of pixels of the image sensor 33 in the horizontal direction and the number of pixels of the image sensor 33 in the vertical direction.

In addition, the image processing unit 42 generates image data on the basis of the extracted pixel signals. Here, the image data is data that is constituted by a plurality of pieces of pixel data and constitutes a color image of the observation target 1. Moreover, the pixel data is data for displaying one pixel (display pixel) in the image and includes RGB luminance information and the like.

For example, the plurality of pieces of pixel data is generated from a plurality of pixel signals as appropriate in accordance with the array of the color filters shown in FIG. 3 and the image data is generated. A method of generating the image data and the like are not limited, and debayering, demosaicing, and the like may be used as appropriate. An arbitrary method of converting RAW data obtained in the other Bayer arrays into a color image or the like may be used.

As described above, in the image processing unit 42, in a state in which the polarization light beam having the incident polarization angle θ is emitted, the image data of the observation target 1 detected on the basis of the polarization component substantially orthogonal to the incident polarization angle θ is generated. Moreover, four types of incident polarization angles θ (0°, 22.5°, 45°, and 67.5°) can be set in the microscope device 100. Therefore, the image processing unit 42 generates each of four pieces of image data different in the incident polarization angle θ. With this configuration, it is possible to realize substantially crossed nicols observation with respect to the observation target 1. It should be noted that in the present disclosure, "substantially crossed" encompasses "crossed". Hereinafter, the substantially crossed nicols observation will be simply referred to as crossed nicols observation.

The analysis unit 43 calculates biological tissue information with respect to the observation target 1 on the basis of the extracted pixel signals. Specifically, the biological tissue information is calculated by analyzing the four pieces of image data generated by the image processing unit 42.

In addition, the analysis unit 43 generates an intraoperative image of the observation target 1 on the basis of the analysis result of the image signal, the calculated biological tissue information, and the like. The intraoperative image is an image of the observation target 1 captured during surgery including observation, treatment, and the like performed by using the microscope device 100.

As described above, in this embodiment, the image processing unit 42 and the analysis unit 43 calculate the biological tissue information regarding the biological tissue on the basis of the pixel signals respectively output from the four pixels 35a to 35d that constitutes the one group. In this embodiment, the image processing unit 42 and the analysis unit 43 cooperate such that the calculation unit is realized.

The display unit 50 displays the intraoperative image of the observation target 1 generated by the analysis unit 43. For example, a display device such as a liquid crystal monitor is used as the display unit 50. For example, the display unit 50 is installed in a room where microscope observation is performed. This makes it possible for a doctor to perform observation and treatment while watching the intraoperative image displayed on the display unit 50. The specific configuration of the display unit 50 is not limited. For example, as the display unit 50, it is possible to use a head-mounted display (HMD) or the like capable of displaying the intraoperative image.

Figure 5:
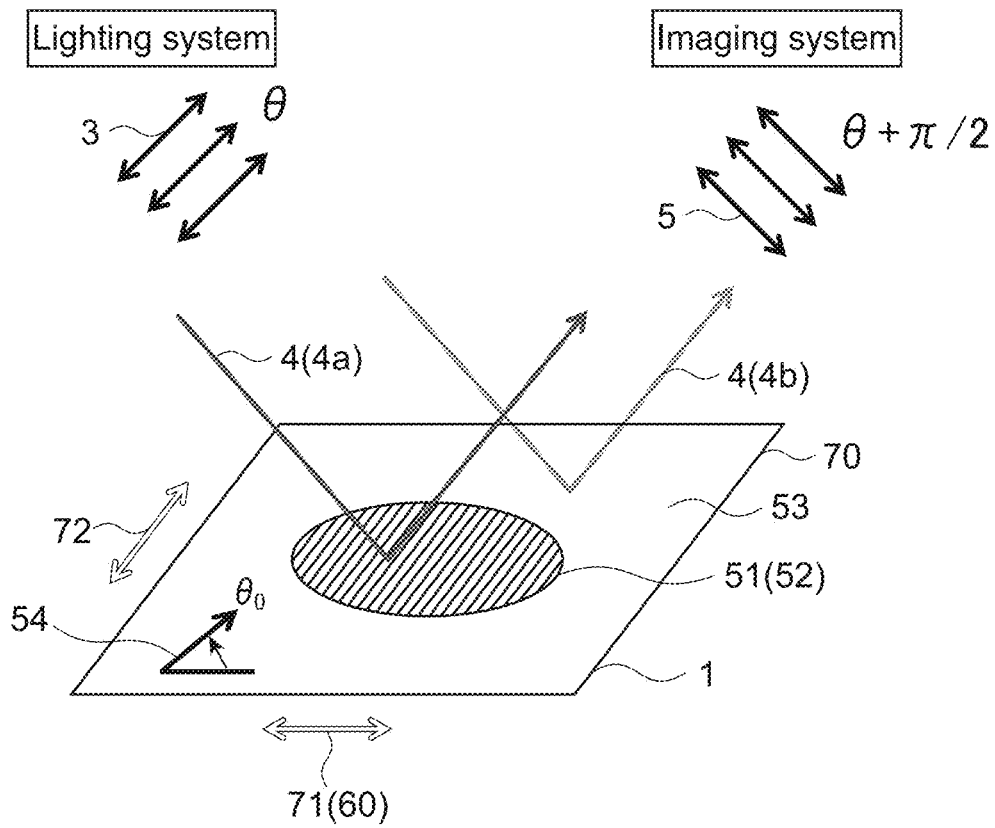
FIG. 5 A schematic view showing an example of crossed nicols observation.
Figure 6A:
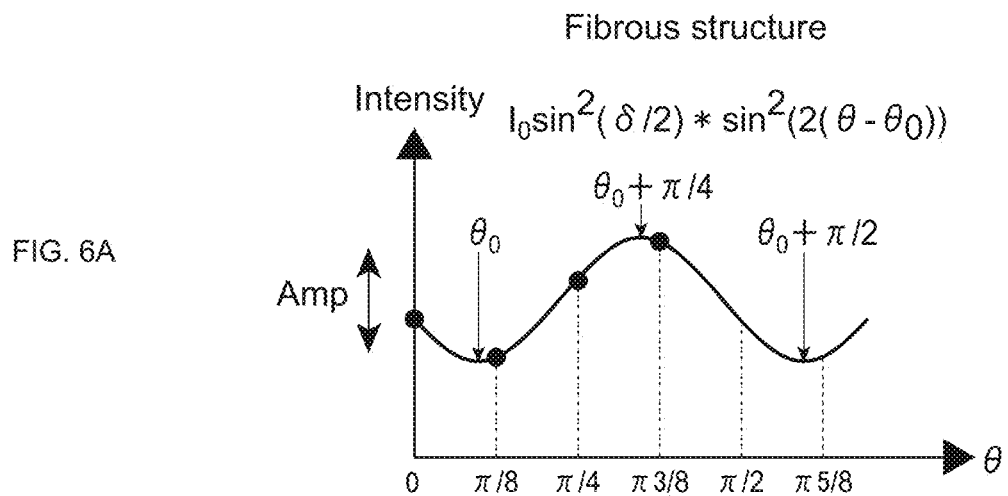
FIGS. 6A and 6B Diagrams showing an example of a result of observation of crossed nicols observation.
Figure 6B:
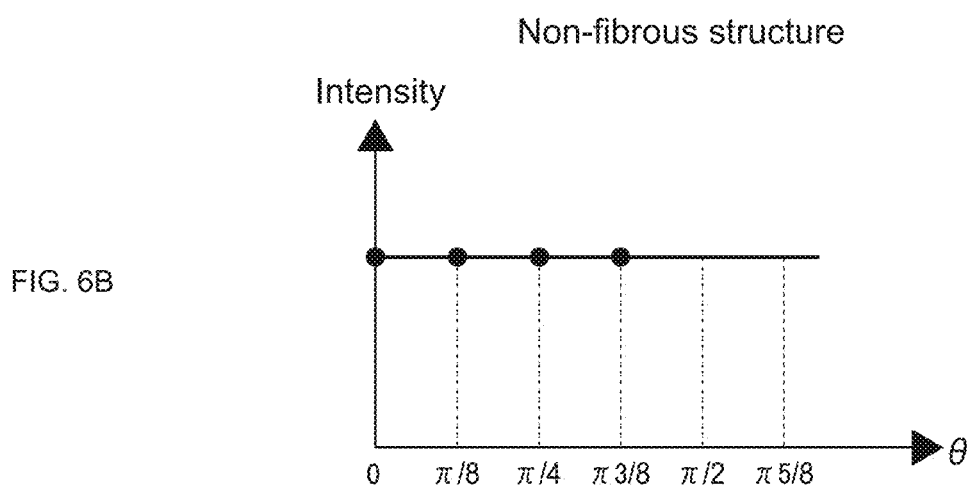

FIG. 5 is a schematic view showing an example of crossed nicols observation. FIGS. 6A and 6B are diagrams showing an example of a result of observation of crossed nicols observation. Hereinafter, observation of the biological tissue (the observation target 1) using crossed nicols observation will be described with reference to FIGS. 5, 6A, and 6B.

FIG. 5 schematically shows an imaging area 70 captured by the polarization camera 32, the left and right directions 71 (the X-axis) of the imaging area 70, and the upper and lower directions 72 (the Y-axis) orthogonal to the left and right directions 71. The imaging area 70 is set to include a region a part of an operative field in surgery, for example. Therefore, the imaging area 70 includes a biological tissue that is the observation target 1. It should be noted that the left and right directions 71 of the imaging area 70 are directions substantially orthogonal to the polarization transmission axis 38 having the transmission angle 90° (see FIG. 2 or FIG. 3). Therefore, the left and right directions 71 of the imaging area 70 are substantially parallel to the polarization direction (the reference direction 60) of the polarization light beam 3 emitted from the lighting polarizer 25a.

In addition, FIG. 5 schematically shows polarization light beams 3 emitted from the lighting system 20, reflection light beams 4 reflected by the observation target 1, and polarization component 5 detected by the polarization camera 32 in crossed nicols observation. It should be noted that the illustration of the lighting system 20 and the imaging system 30 has been omitted from FIG. 5.

In the example shown in FIG. 5, it is assumed that the polarization light beams 3 having the incident polarization angle θ are emitted and the polarization components 5 of the reflection light beams 4 from the observation target 1, which have a polarization direction of θ+π/2, are extracted. In the reality, the polarization light beams 3 each having incident polarization angles θ of 0°, 22.5°, 45°, or 67.5° are sequentially emitted and the polarization components 5 substantially orthogonal to the emitted polarization light beams 3 are detected as appropriate.

Some of the polarization light beams 3 that have been incident upon the observation target 1 are reflected in the vicinity of the surface of the observation target 1 (the illustration is omitted). In reflection in the vicinity of the surface of the observation target 1, the polarization states are substantially retained before and after reflection. Therefore, the polarization light beams 3 reflected in the vicinity of the surface travel, to the imaging system 30, the reflection light beams 4, which have been influenced by the characteristics in the vicinity of the surface, while maintaining the polarization directions at the time of incidence.

Since the reflection light beams 4 in the vicinity of the surface maintain the polarization directions (the incident polarization angles θ) before reflection, the reflection light beams 4 hardly pass through the light-receiving polarizers 37 whose transmission angles are θ+π/2. Therefore, in the pixels 35 in which the light-receiving polarizers 37 whose transmission angles are θ+π/2 are arranged, the reflection light beams 4 from the vicinity of the surface are hardly detected. Therefore, in crossed nicols observation, the observation target 1 can be observed while reducing influences of reflection (specular reflection or the like) that occurs on the surface of the observation target 1.

Meanwhile, the other parts of the polarization light beams 3 that have been incident upon the observation target 1 are incident upon the inside of the observation target 1. In the inside of the observation target 1, various biological tissues such as fat and muscle exist. The polarization light beams 3 incident upon the inside of the observation target 1 experience diffusion, scattering, absorption, rotation of the polarization direction, or the like in a manner that depends on the optical characteristics of the respective biological tissues. As a result, the reflection light beams 4 that have experienced multiplex scattering in the inside of the observation target 1 includes polarization components of various polarization directions.

As shown in FIG. 5, the observation target 1 includes a fibrous tissue 52 that is an anisotropic object 51 and a non-fibrous tissue 53. Here, the anisotropic object 51 is an optically anisotropic biological tissue, for example. Examples of the anisotropic object 51 of the biological tissue include muscle fibers of muscle, collagen fibers in cartilage such as a meniscus, and a nerve fascicles that are bundles of nerve fibers. As a matter of course, the present technology is not limited thereto. The present technology is applicable to any optically anisotropic tissue and the like.

For example, when the polarization light beam 3 is emitted to the anisotropic object 51, the polarization state changes in accordance with the optical characteristics of the anisotropic object 51. For example, due to linear birefringence of the anisotropic object 51, a polarization direction of the polarization light beam 3 is rotated. In addition, due to linear dichroism of the anisotropic object 51, some polarization components of the polarization light beam 3 are absorbed and the polarization light beam 3 is polarized as an elliptically polarization light beam. As a result, the anisotropic object 51 emits a reflection light beam 4a in the polarization state different from that of the polarization light beam 3 emitted to the anisotropic object 51.

In addition, the polarization states of the reflection light beam 4a such as the polarization direction and ellipticity change in accordance with the polarization direction (the incident polarization angle θ) of the polarization light beam 3 that has been emitted. In other words, the polarization state, intensity, and the like of the reflection light beam 4a change in accordance with optical characteristics of the anisotropic object 51 and the polarization direction of the polarization light beam 3 emitted to the anisotropic object 51.

The reflection light beam 4a reflected by the anisotropic object 51 is incident upon the imaging system 30 (the light-receiving polarizer 37). The light-receiving polarizer 37 extracts the polarization component 5 of the polarization components included in the reflection light beam 4a, whose polarization direction is parallel to the polarization transmission axis 38 of the light-receiving polarizer 37, and causes the polarization component 5 to be incident upon the pixel 35 at the subsequent stage. Hereinafter, in a state in which the incident polarization angle θ and the transmission angle φ are in a crossed nicols relationship, the intensity of the polarization component 5 extracted by the light-receiving polarizer 37 will be referred to as first intensity.

In a case where the anisotropic object 51 is observed in the state in which the incident polarization angle θ and the transmission angle φ are in the crossed nicols relationship, the first intensity is calculated in accordance with the following equation by using the incident polarization angle θ.

$$I_0 * \sin^2(\delta/2) * \sin^2(2(\theta - \theta_0)) \quad (1)$$

Where I0 denotes the intensity of the polarization component extracted in the state in which the incident polarization angle θ and the transmission angle φ are in a parallel nicols relationship (θ=φ). I0 denotes a value depending on a variation in fiber direction, i.e., orientation of the anisotropic object 51, for example. Moreover, δ denotes a phase difference caused by the anisotropic object 51 and is a value depending on the optical characteristics of the anisotropic object 51 and the like. Moreover, $\theta_0$ denotes a phase component and corresponds to the fiber direction 54 of the anisotropic object 51. It should be noted that the fiber direction 54 of the anisotropic object 51 is a direction in which the fibrous tissue 52 that constitutes the anisotropic object 51, for example, extends.

The graph of FIG. 6A is a graph showing an example of the first intensity. FIG. 6A shows the intensity of the polarization component 5 extracted from the reflection light beam 4 reflected on the anisotropic object 51. The horizontal axis of the graph indicates the incident polarization angle $\theta$ and the vertical axis indicates the intensity of the polarization component 5.

As described in Equation (2), the first intensity is the periodic function that fluctuates with a cycle of 90° with respect to the incident polarization angle $\theta$. It should be noted that in the graph of FIG. 6A, the first intensity includes an offset due to randomization or the like of the polarization direction due to multiple reflection caused inside the observation target 1.

As shown in FIG. 6A, the first intensity is minimum at $\theta_0$. In addition, the first intensity is maximum at $\theta_0+\pi/4$ and is minimum again at $\theta_0+\pi/2$. In this manner, the incident polarization angle $\theta$ is increased from 0°, and the initial value with which the first intensity is minimum is the phase component $\theta_0$.

In a case where the direction parallel to the incident polarization angle $\theta$ and the fiber direction 54 of the anisotropic object 51 are parallel or orthogonal, the first intensity is minimum. Therefore, the phase component $\theta_0$ indicates the direction orthogonal or parallel to the fiber direction 54 of the anisotropic object 51. In this manner, the information regarding the phase component $\theta_0$ is information regarding the fiber direction 54 (the orientation direction) of the anisotropic object 51.

In addition, the amplitude of the first intensity Amp is $I_0 \sin^2(\delta/2)$. This amplitude Amp is expressed by the value ($I_0$) according to the orientation of the anisotropic object 51 and the value ($\delta$) according to the optical anisotropy of the anisotropic object 51. In this manner, the information regarding the amplitude Amp is information regarding the orientation of the anisotropic object 51 and the anisotropy.

It should be noted that in this embodiment, crossed nicols observation is performed by using four types of polarization light beams 3 different in the incident polarization angle $\theta$. That is, for each of the four types of polarization light beams 3, the first intensity is detected and four data points are detected. FIG. 6A shows a data point at which the incident polarization angle $\theta$ is 0°, a data point at which the incident polarization angle $\theta$ is 22.5° ($\pi/8$), a data point at which the incident polarization angle $\theta$ is 450 ($\pi/4$), and a data point at which the incident polarization angle $\theta$ is 67.5° ($\pi 3/8$). For example, it is possible to calculate the phase component $\theta_0$, the amplitude Amp, and the like by fitting the function shown in Equation (1) to those data points.

The graph of FIG. 6B is a graph showing another example of the first intensity detected in crossed nicols observation. The reflection light beam 4b reflected by the non-fibrous structure 53 does not have a particular polarization direction and the polarization direction is randomized. Therefore, the reflection light beam 4b includes a substantially constant proportion of the polarization component 5 of the polarization direction at the transmission angle $\varphi$ irrespective of the value of the incident polarization angle $\theta$.

As shown in the graph of FIG. 6B, substantially constant first intensity is detected irrespective of the incident polarization angle $\theta$ in a case of carrying out crossed nicols observation of the non-fibrous structure 53. Therefore, with the non-fibrous structure 53, the periodic change in first intensity as shown in FIG. 6A is not detected. It should be noted that a change in first intensity is substantially zero in a case where a structure in which double refraction is not caused or a region or the like having large specular reflection, which is covered with body fluid, is observed.

As described above, in a case where the first intensity changes with a cycle of $\pi/2$ with respect to the incident polarization angle $\theta$, it is highly likely that the anisotropic object 51 is being observed. In contrast, in other cases, it is highly likely that the non-fibrous structure 53 is being observed. Therefore, it is possible to calculate identification information for identifying whether or not the observation target 1 includes the anisotropic object 51 by sequentially emitting the polarization light beam 3 different in the incident polarization angle $\theta$ and analyzing the change in first intensity according to the rotation operation.

Hereinafter, observation of the observation target 1 will be described specifically.

Figure 7:
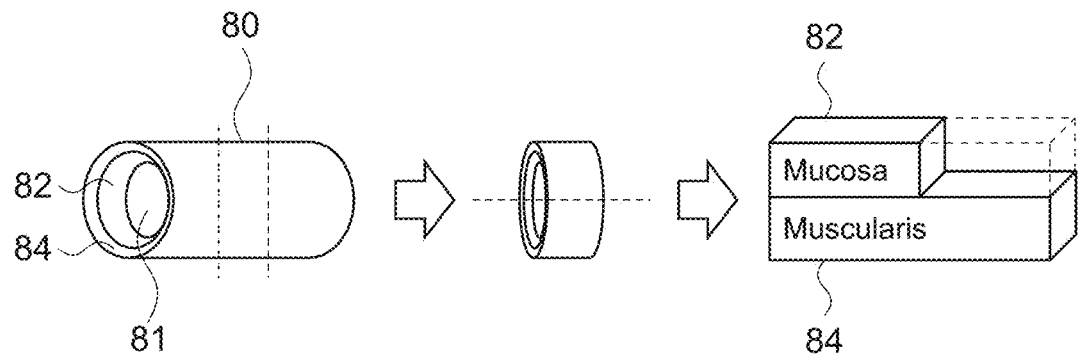
FIG. 7 A schematic view for describing an observation target.
Figure 8:
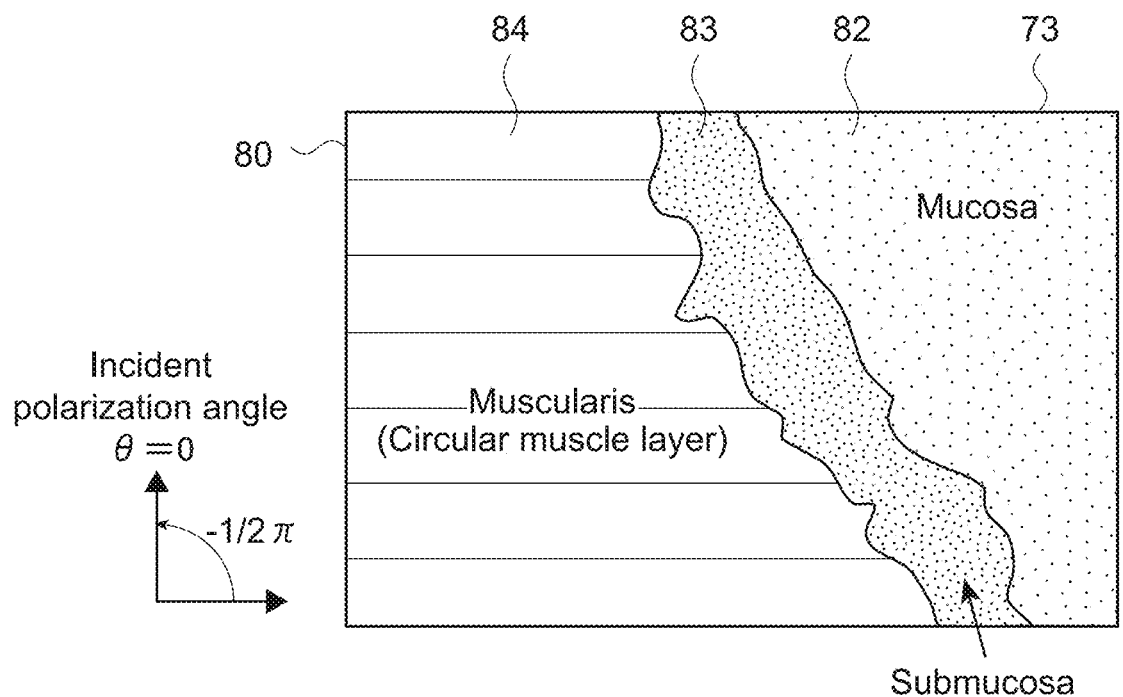
FIG. 8 A schematic view showing an example of an image of the observation target imaged in crossed nicols observation.

FIG. 7 is a schematic view for describing the observation target 1. FIG. 8 is a schematic view showing an example of an image of the observation target 1 imaged in crossed nicols observation. Hereinafter, the description will be given by showing a rectum of a pig as an example of the observation target 1.

Figure 10A:
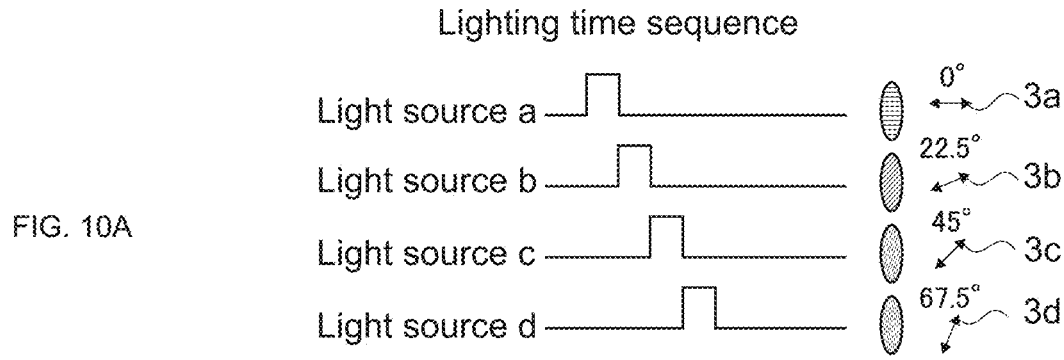
FIGS. 10A and 10B Schematic views showing an example of a time sequence of biological tissue observation.
Figure 10B:
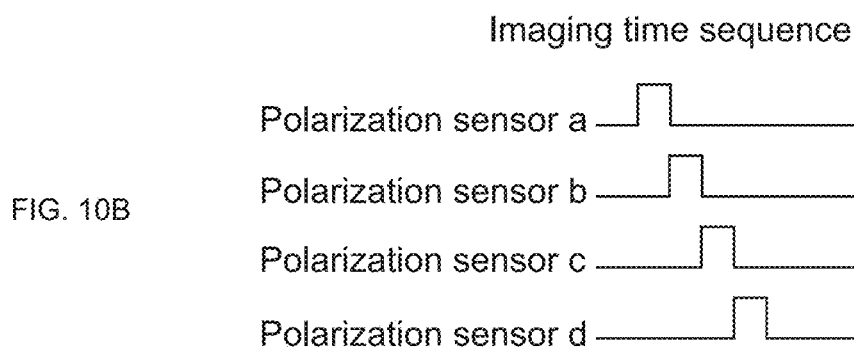

FIGS. 10A and 10B schematically show a rectum 80 of a pig. The rectum 80 is a tubular structure and has a lumen 81. Digested food and the like pass through the lumen 81. The rectum 80 includes a mucosa 82, a submucosa 83, and a muscle layer 84 (muscularis) from the inside (from the lumen 81 side). FIGS. 10A and 10B schematically show the mucosa 82 and the muscle layer 84 that constitute the rectum 80. It should be noted that the illustration of the submucosa 83 is omitted.

The inside of the muscle layer 84 is constituted by a circular muscle layer and the outside of the circular muscle layer is constituted by a longitudinal muscle layer. Muscle fibers that constitute the circular muscle layer are oriented in a direction substantially orthogonal to a direction in which the rectum 80 extends. In other words, a muscle fiber direction of the circular muscle layer is a direction along the inner periphery surrounding the lumen 81. In addition, muscle fibers that constitute the longitudinal muscle layer are oriented in a direction substantially parallel to the direction in which the rectum 80 extends.

As shown in FIGS. 10A and 10B, a part of a tubular structure is cut out by cutting the rectum 80. The mucosa 82 inside the rectum 80 is exposed by incising the cut-out rectum 80. Then, the muscle layer 84 is exposed by peeling off a part of the exposed mucosa 82. FIGS. 10A and 10B schematically show the pealed-off mucosa 82 as the dotted lines. At this time, the circular muscle layer can be seen through the exposed portion of the muscle layer 84. This mucosa 82 and the site at which the circular muscle layer (the muscle layer 84) is exposed are used as the observation target 1. Hereinafter, the exposed circular muscle layer will be simply referred to as the muscle layer 84.

FIG. 8 schematically shows an observation image 73 of the pig's rectum 80 (the observation target 1) imaged in crossed nicols observation. The observation image 73 includes the exposed muscle layer 84 (the circular muscle layer) and the mucosa 82. In addition, the submucosa 83 is present at the boundary between the muscle layer 84 and the mucosa 82. It should be noted that FIG. 8 schematically shows the muscle fiber direction of the muscle layer 84 as the oblique lines and the submucosa 83 and the mucosa 82 as the dots. No oblique lines, dots, and the like are displayed in the actual observation image 73.

As the observation image 73, the rectum 80 is imaged such that the muscle fiber direction 54 of the exposed muscle layer 84 is a direction extending in the left and right directions of the observation image 73. The left and right directions of the observation image 73 are directions similar to the left and right directions 71 of the imaging area 70 shown in FIG. 5. Therefore, for example, in a case where the incident polarization angle θ is 0 (the reference direction 60), the emitted polarization light beam 3 and the first polarization direction 29 and the muscle fiber direction of the muscle layer 84 are substantially parallel to each other and the intensity (the first intensity) of the polarization component 5 detected in crossed nicols observation is minimum.

In addition, for example, the state in which the incident polarization angle θ is π/4 corresponds to the state of $θ_0+π/4$. In this manner, the first intensity is a periodic function that fluctuates with a cycle of π/2 and is a maximum value at an angle of the phase component $θ_0±π/4$. Therefore, in the state of the incident polarization angle θ=π/4, the intensity of the polarization component 5 similar to the maximum value in $θ_0+π/4$ shown in the graph of FIG. 6A is detected. Hereinafter, imaging of the observation target 1 (the rectum 80) is performed in the arrangement shown in FIG. 8.

Figure 9:
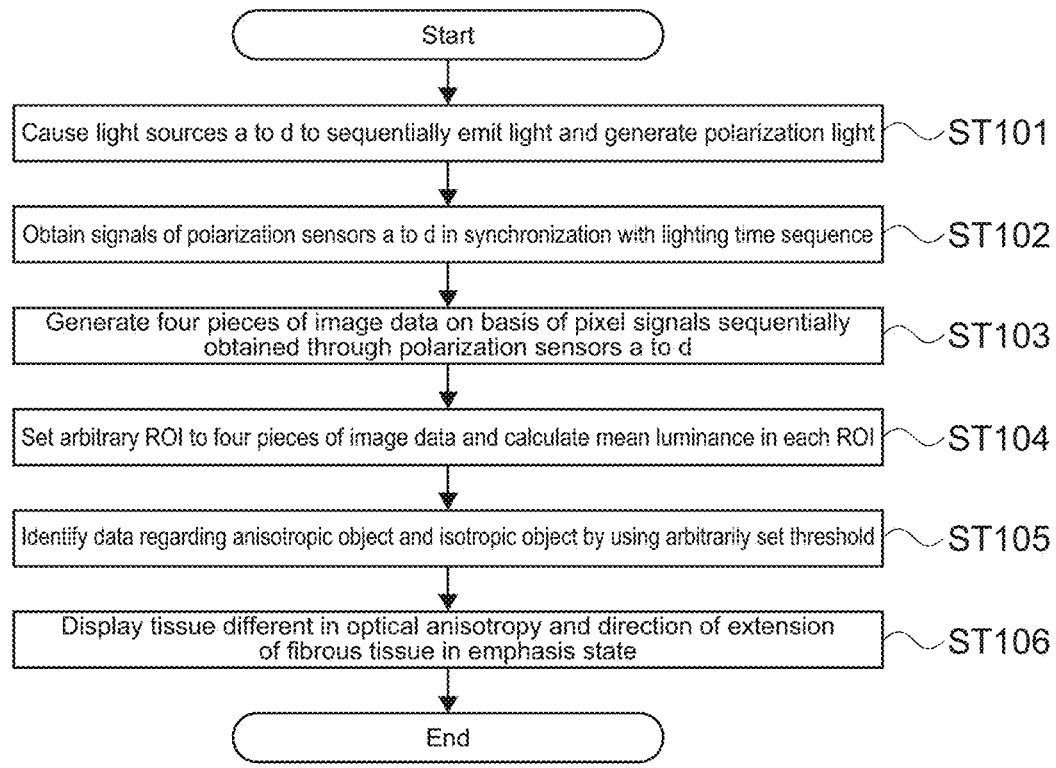
FIG. 9 A flowchart showing an example of biological tissue observation.

FIG. 9 is a flowchart showing an observation example of the biological tissue. FIGS. 10A and 10B are schematic views showing an example of a time sequence of biological tissue observation. The processing shown in FIG. 9 is, for example, processing that is started when the microscope device 100 starts observation of the biological tissue (the observation target 1) and that is repeatedly performed until the observation ends.

The light sources 24a to 24d are made to sequentially emit light beams and four types of polarization light beams different in the incident polarization angle θ are generated (Step 101). FIG. 10A is a schematic view showing a time sequence indicated by the timings of light emission of the respective light sources 24a to 24d. In this embodiment, the light sources 24a to 24d are made to sequentially emit light beams in the stated order.

For example, the emission control unit 41 outputs a start signal for instructing the light source 24a to start emission of the emission light beam. The light source 24a that has received the start signal emits the emission light beam. The emission light beam is incident upon the lighting polarizer 25a via the light guide and the lighting polarizer 25a emits a polarization light beam 3a of the polarization direction parallel to the reference direction 60, i.e., the polarization light beam 3a having the incident polarization angle 0° (see FIG. 1).

Moreover, when a predetermined period (emission period) has elapsed from the timing at which the start signal is output, the stop signal for instructing the light source 24a to stop emission of the emission light beam is output and the light emission of the light source 24a is stopped. The emission period is set as appropriate such that the polarization camera 32 can appropriately perform imaging, for example.

When the light emission of the light source 24a stops, the light source 24b is made to emit a light beam for a predetermined period and the lighting polarizer 25b emits a polarization light beam 3b having the incident polarization angle of 22.5°. Moreover, when the light emission of the light source 24b stops, the light source 24c is made to emit a light beam for a predetermined period and the lighting polarizer 25c emits a polarization light beam 3c having the incident polarization angle of 45°. Then, when the light emission of the light source 24c stops, the light source 24d is made to emit a light beam for a predetermined period and the lighting polarizer 25d emits a polarization light beam 3d of the incident polarization angle of 67.5°.

As described above, the lighting system 20 sequentially emits the plurality of polarization light beams 3a to 3d whose respective polarization directions are included in an angle range between the reference direction 60 and the orthogonal direction orthogonal to the reference direction 60. With this configuration, it is possible to realize crossed nicols observation in an angle range in which the incident polarization angle θ is 90° or less. As a result, it is possible to accurately perform fitting or the like with respect to the first intensity (see FIG. 6A) or the like that fluctuates with a cycle of 90° with respect to the incident polarization angle θ.

It should be noted that the respective light sources 24a to 24d are made to sequentially emit light beams with no intervals after the respective emission periods end. With this configuration, it is possible to sufficiently shorten the time necessary for imaging. It should be noted that the emission period of the light source 24, the timing of light emission, and the like, are not limited. For example, an interval may be provided between the emission periods of the light source 24. Moreover, the emission period may be set in accordance with the frame rate and the exposure-to-light condition of the polarization camera 32, the processing speed of the controller 40, and the like.

The pixel signals corresponding to the polarization light beams 3a to 3d are obtained in synchronization with the lighting time sequence (Step 102). FIG. 10B is a schematic view showing a time sequence representing imaging timings. FIG. 10B schematically shows the time sequence of imaging synchronized with the lighting time sequence of FIG. 10A. In this embodiment, the polarization camera 32 performs imaging processing on the observation target 1 when each of the respective polarization light beams 3a to 3d is emitted.

It should be noted that the imaging processing is, for example, a process of extracting pixel signals from a plurality of polarization cameras 32 to which similar transmission angles φ are set and generates image data on the basis of the extracted pixel signals.

For example, a pixel signal of the polarization sensor 39a having the transmission angle of 90° is obtained in accordance with the emission period of the polarization light beam 3a having the incident polarization angle 0°. That is, crossed nicols observation at the incident polarization angle of 0° is performed. For example, a pixel signal of the polarization sensor 39a (a pixel 35a) is extracted from output data of image sensor 33 exposed to light is obtained in accordance with the emission period of the polarization light beam 3a. It should be noted that the start and end timings and the like of exposure-to-light at the image sensor 33 are controlled on the basis of a synchronization signal output from the emission control unit 41, for example.

Similarly, a pixel signal of the polarization sensor 39b having a transmission angle of 112.5° is obtained in accordance with the emission period of the polarization light beam 3b having the incident polarization angle of 22.5°. Moreover, a pixel signal of the polarization sensor 39c having a transmission angle of 135° is obtained in accordance with the emission period of the polarization light beam 3b having the incident polarization angle of 45°. Then, a pixel signal of the polarization sensor 39d having a transmission angle of 157.5° is obtained in accordance with the emission period of the polarization light beam 3d having the incident polarization angle of 67.5°.

Four pieces of image data is generated on the basis of the pixel signals sequentially obtained by using the polarization sensors 39a to 39d (Step 103). The creation of the image data is sequentially performed every time when a pixel signal is obtained by using the respective polarization sensors 39a to 39d, for example. Not limited thereto, a process of generating the four pieces of image data at a timing at which all pixel signals are obtained may be performed.

As described above, in the microscope device 100, four crossed nicols images (image data) are sequentially generated in the state in which the polarization direction of the emitted polarization light beam 3 (the incident polarization angle θ) and the polarization direction (the transmission angle T) of the detected polarization component 5 are substantially orthogonal to each other. That is, it can also be said that crossed nicols observation is performed four times while changing the incident polarization angle θ in steps of 22.5°.

Figure 11:
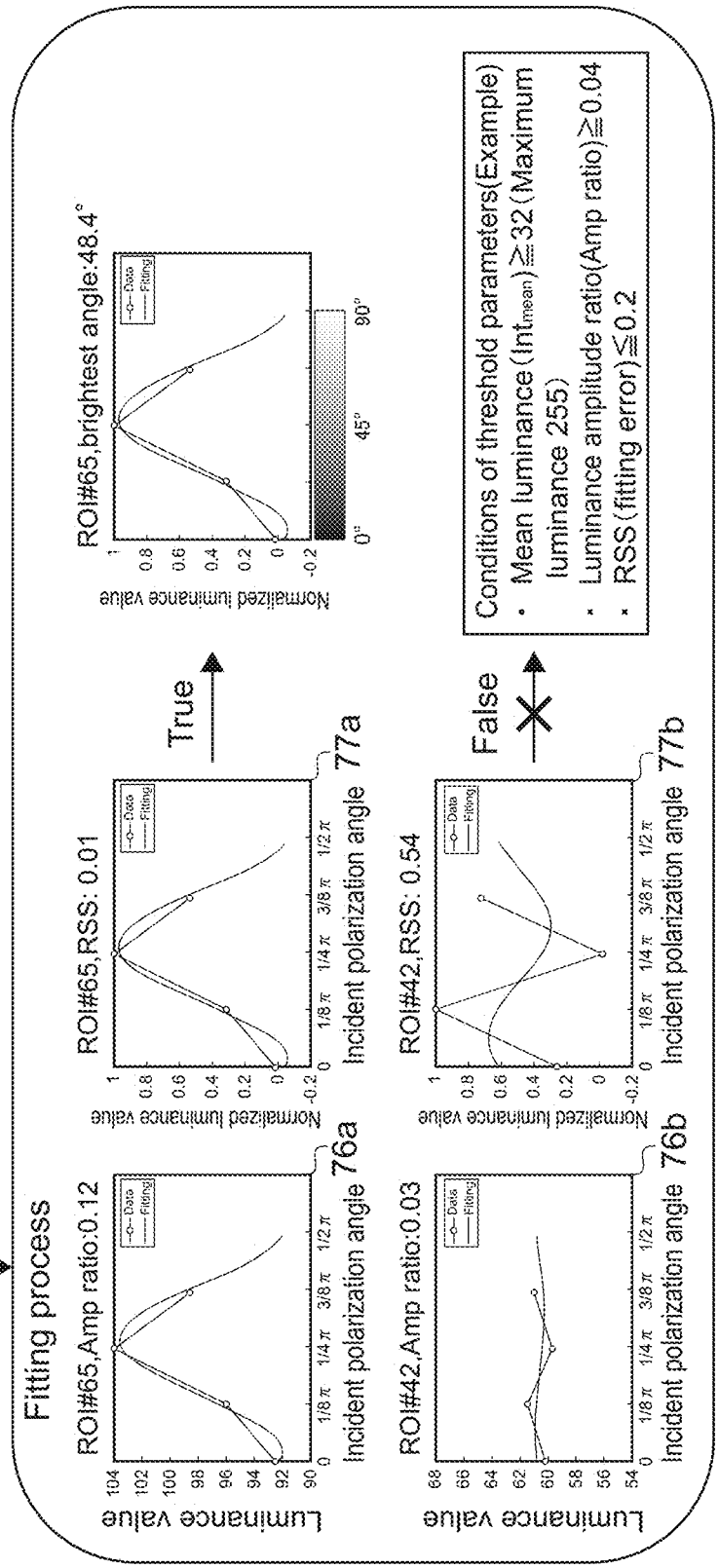
FIG. 11 A diagram for describing an example of a process of calculating the biological tissue information on the basis of image data generated in crossed nicols observation.
Figure 12:
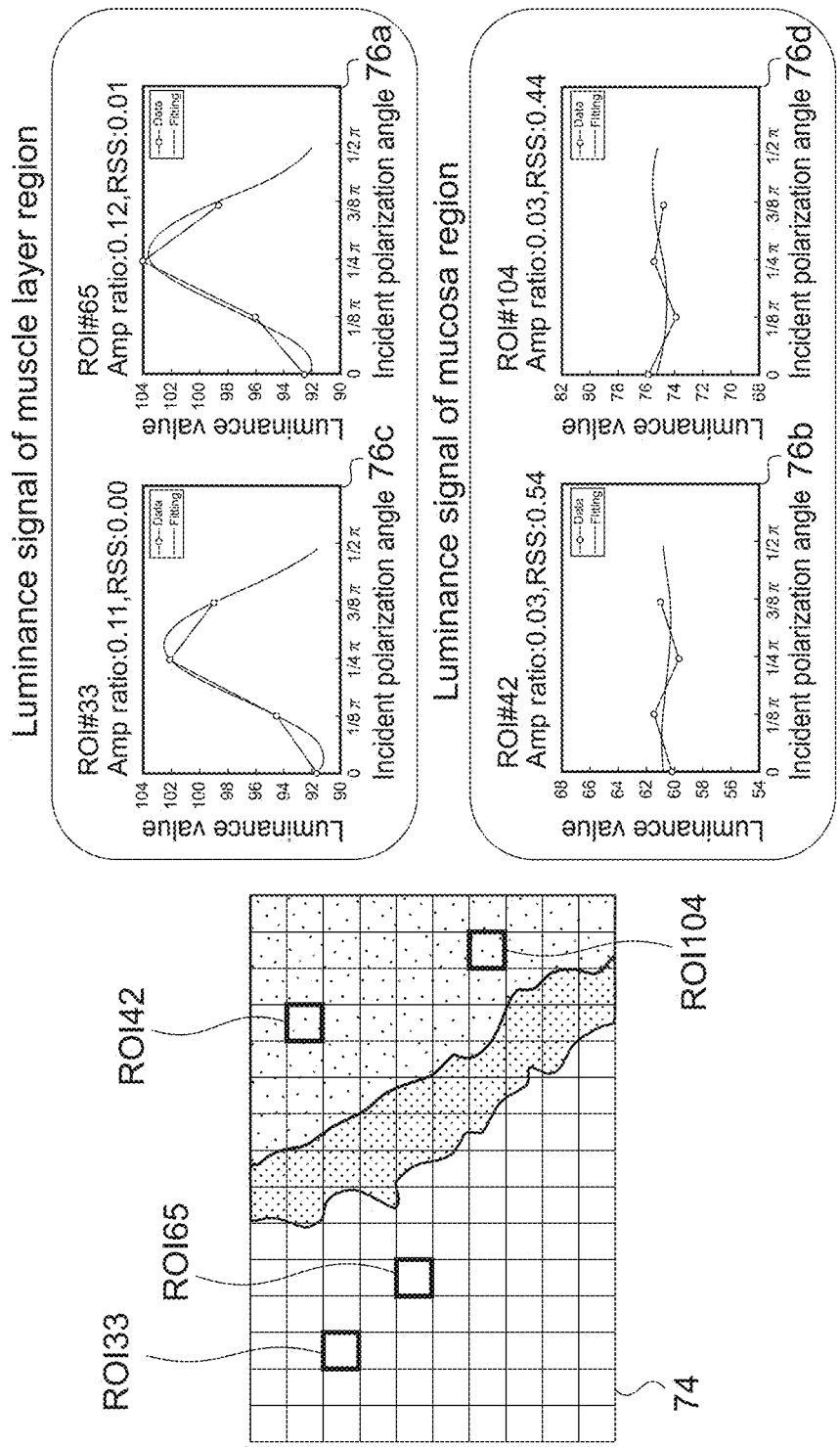
FIG. 12 A diagram showing a specific example of a process of calculating the biological tissue information shown in FIG. 11.

FIG. 11 is a diagram for describing an example of a process of calculating the biological tissue information on the basis of the image data generated in crossed nicols observation. FIG. 12 is a diagram showing a specific example of the process of calculating the biological tissue information shown in FIG. 11.

FIG. 11 sequentially shows respective processes for calculating the biological tissue information on the basis of the image data 74 (the observation image 73). The image signal generated in Step 103 is output to the analysis unit 43. The analysis unit 43 detects the first intensity for each pixel of the image data 74. Here, a process of converting the RGB value of each pixel into the gray scale is performed and a luminance value indicated by the gradation of gray scale is detected as the first intensity. As a matter of course, the following calculation may be performed for each RGB channel without conversion into the gray scale.

The analysis unit 43 sets a plurality of analysis regions (ROIs), into which the observation image 73 constituted by the image data 74 is to be divided, and calculates biological tissue information with respect to each of the plurality of analysis regions. In this embodiment, the analysis regions correspond to target regions. Hereinafter, the analysis region will be referred to as an ROI 75.

First of all, the analysis unit 43 sets the ROI 75 having a predetermined size with respect to each image signal converted into the gray scale and calculates a mean luminance in the ROI 75 (Step 104).

The size of the ROI 75 can be set as appropriate in accordance with the resolution and the like for observing the observation target 1, for example. In this embodiment, the ROI 75 of 30 pixels×30 pixels is used. As a matter of course, not limited thereto, the ROI 75 having a desired size may be set as appropriate.

The analysis unit 43 calculates the average value (the mean luminance) of the first intensity of the pixels included in the ROI 75 for each set ROI 75. FIG. 11 schematically shows pixels included in one ROI 75 and its luminance value $A_{m,n}$. It should be noted that m and n are integers from 1 to 30 and are indicators representing the position of each pixel within the ROI. An average value of the first intensity is calculated by dividing the sum in the ROI 75 of this luminance value $A_{m,n}$ by the number of pixels (30×30) in the ROI 75.

The process of calculating the average value of the first intensity of the ROI 75 is performed on each of the four pieces of image data 74 (the observation image 73). Therefore, an average value of the first intensity in a case where the incident polarization angle θ is 0, 22.5°, 45°, or 67.5° is calculated for each ROI. In this manner, data regarding the average value of the first intensity according to the incident polarization angle θ calculated for each ROI 75 is used as first intensity data representing a change in first intensity due to a change in incident polarization angle θ.

FIG. 11 shows graphs 76a and 76b of the first intensity data calculated at the ROI #65 and the ROI #42. The horizontal axis of each graph indicates the incident polarization angle θ and the vertical axis indicates a luminance value. It should be noted that the vertical axes of the graphs 76a and 76b are set to have a common width (14) and the amplitude and the like of each graph can be directly compared.

In this embodiment, the luminance amplitude ratio (Amp ratio) is calculated as the amplitude of the first intensity data. The luminance amplitude ratio is a value obtained by dividing the difference (the amplitude) between the maximum value and the minimum value of four data points (the average value of the first intensity within the ROI) by an average value $I_{average}$ of the four data points.

As shown in FIG. 11, in the ROI #42, the luminance value does not greatly change even when the incident polarization angle θ changes. Therefore, it can be seen that the mucosa 82 exists at the position at which the ROI #42 is set. The luminance amplitude ratio calculated in the ROI #42 is 0.03.

The luminance ratio in the ROI #65 is a periodic function that fluctuates with a cycle of π/2 (90°) with respect to the incident polarization angle θ. Therefore, it can be seen that the muscle layer 84 exists at the position at which the ROI #65 is set (see FIG. 12). In addition, the luminance amplitude ratio calculated for the ROI #65 is 0.12 and takes a sufficiently large value in comparison with the ROI #42 on the mucosa 82.

The analysis unit performs a fitting process using a predetermined function with respect to the first intensity data. FIG. 11 shows graphs 77a and 77b which are results of the fitting process on the first intensity data calculated for the ROI #65 and the ROI #42. The horizontal axis of the graph 77a or 77b indicates the incident polarization angle θ and the vertical axis indicates a luminance value normalized at the maximum value (normalized luminance value).

In this embodiment, a predetermined function $f(\theta)=A\times \sin^{2}(2(\theta-B))+C$ is set by using the function described in Equation (1) as a reference. Parameters A and B are parameters representing amplitude information and phase information of the predetermined function f(θ). Therefore, it can also be said that the parameters A and B are parameters corresponding to the amplitude Amp and the phase component $\theta_0$ of Equation (1). In this embodiment, the predetermined function f(θ) corresponds to a predetermined periodic function. It should be noted that the parameter C is a parameter representing an amount of offset of the predetermined function f(θ).

In the fitting process, such parameters A and B that the predetermined function f(θ) fits the first intensity data are calculated. In addition, a residual sum of squares (RSS) is calculated as a parameter for assessing the discordance between the predetermined function f(θ) and the first intensity data. It should be noted that a specific method and the like for the fitting process are not limited, and a process using a least squares method or the like, for example, may be performed as appropriate.

As shown in FIG. 11, the predetermined function f(O) is hardly fitted to the first intensity data calculated for the ROI

42. As a result of the fitting process for the ROI #42, the calculated residual sum of squares is 0.54.

On the other hand, such parameters A and B that the predetermined function f(O) can be sufficiently fitted to the first intensity data calculated for the ROI #65 are calculated. The result of the fitting process for the ROI #65, the residual sum of squares is 0.01. It means that the ROI #65 is in accord with the predetermined function f($\theta$) more sufficiently than the ROI #42.

Therefore, the amplitude Amp and the phase component $\theta_0$ of the periodic function expressed by Equation (1) can be calculated by calculating the parameters A and B in the ROI #65 including the anisotropic object 51 (the muscle layer 84). As shown in described in the graph of FIG. 6A, the information regarding the phase component $\theta_0$ is the information regarding the orientation direction of the anisotropic object 51. In addition, information regarding the amplitude Amp is information regarding the orientation of the anisotropic object 51 and the anisotropy.

FIG. 12 shows graphs 76c and 76d showing first intensity data for other ROI #33 and ROI #104. In the graph 76c for the ROI #33, the amplitude of the luminance value is large and the calculated luminance amplitude ratio is 0.11. Moreover, each data point is sufficiently fitted to the predetermined function f($\theta$) and the calculated residual sum of squares is 0.00. Therefore, it can be seen that the muscle layer 84 exists at the position at which the ROI #33 is set as in the ROI #65.

In the graph 76d for the ROI #104, the amplitude of the luminance value is small and the calculated luminance amplitude ratio is 0.03. Moreover, the respective data points are hardly fitted and the calculated residual sum of squares is 0.44. Therefore, it can be seen that the mucosa 82 exists at the position at which the ROI #104 is set as in the ROI #42.

As described above, the analysis unit 43 performs the fitting process using the predetermined function f($\theta$), calculates the information regarding the phase component $\theta_0$ on the basis of phase information B of the predetermined function f($\theta$) which is obtained as a process result of the fitting process, and calculates the information regarding the amplitude Amp on the basis of amplitude information A of the predetermined function f($\theta$). The information regarding the phase component $\theta_0$ and the information regarding the amplitude Amp, which have been calculated, are stored as the biological tissue information after an identification process of the anisotropic object 51 to be described later.

When the fitting process ends, a process of identifying signals of the anisotropic object 51 (the fibrous structure 52) and an isotropic object (the non-fibrous structure 53) using threshold parameters is performed (Step 107). FIG. 11 shows conditions of the threshold parameters. In this embodiment, the mean luminance ($Int_{mean}$), the luminance amplitude ratio (Amp ratio), and the residual sum of squares (RSS) of the ROI 75 are used as the threshold parameters. It should be noted that the threshold parameters can be changed as appropriate in a manner that depends on an imaging condition, an object to be imaged, and the like.

The average value ($I_{average}$) of the four data points, for example, is used as the mean luminance $Int_{mean}$. The mean luminance $Int_{mean}$ is a parameter indicating the brightness of the ROI 75. Therefore, the observation target 1 and the background of the observation target 1 can be identified by comparing the mean luminance $Int_{mean}$ with a predetermined threshold. As shown in FIG. 11, in a case where the luminance value (the first intensity) is expressed by an 8-bit scale 256 gradation, $Int_{mean} \geq 32$ is set for the condition related to the mean luminance to thereby exclude dark portions in the image from analysis. The calculation speed is thus increased.

The luminance amplitude ratio is a parameter indicating the levels of the orientation and the anisotropy. For example, in a case where the luminance amplitude ratio is small, it is highly likely that the orientation and the anisotropy are small and a site which is not the anisotropic object 51 is being observed. On the contrary, in a case where the luminance amplitude ratio is large, it is highly likely that the anisotropic object 51 is being observed. The condition related to the luminance amplitude ratio is set to Amp ratio$\geq 0.04$.

The residual sum of squares is a parameter indicating the degree of accordance between the first intensity data and the predetermined function f($\theta$) as described above. In other words, it can be said that as the residual sum of squares becomes smaller, a fitting error of $\sin^2(2\theta)$ is smaller. In this case, it is highly likely that the first intensity data is a periodic function that fluctuates with a cycle of $\pi/2$ with respect to the incident polarization angle $\theta$. The condition related to the residual sum of squares is set to RSS$\leq 0.2$.

The analysis section 43 identifies whether or not each ROI includes the anisotropic object 51 on the basis of the above-mentioned condition. For example, as shown in FIG. 11, the ROI #65 is determined to satisfy (True) the conditions of the threshold parameters. Therefore, the ROI #65 is identified to include the anisotropic object 51. In addition, for example, the ROI #42 is determined not to satisfy (False) the conditions of the threshold parameters. Therefore, the ROI #42 is identified not to include the anisotropic object 51. Here, the threshold parameters are predicted to be different from an optimum value in a manner that depends on a measurement target, a lighting condition, and the like. Therefore, it is necessary to revise the parameters for correct identification as appropriate.

On the basis of the identification result, the analysis section 43 calculates identification information for identifying whether or not the observation target 1 includes the anisotropic object 51 as the biological tissue information of the observation target 1. In other words, information indicating whether or not each ROI includes the anisotropic object 51 is calculated as the identification information.

As described above, by calculating the identification information, the muscle layer 84 including the anisotropic object 51 and other sites can be identified with high accuracy. In addition, there is a case where a ROI 75 identified not to include the anisotropic object 51 on the muscle layer 84, a ROI 75 identified to include the anisotropic object 51 on the mucosa 82, and the like are calculated. With this configuration, for example, it is also possible to detect a local abnormality or the like in the muscle layer 84 or the mucosa 82.

When the identification process ends, the process result of the fitting process of the ROI 75 identified to include the anisotropic object 51 is stored as the biological tissue information. For example, as shown in FIG. 11, regarding the ROI #65, the phase component $\theta_0$ related to the first intensity data, the amplitude Amp, and the like are stored.

In addition, a value of the incident polarization angle $\theta$ (a maximum luminance angle $\theta_{max}$) with which the luminance value is maximum and the like may be stored, for example. As shown in FIG. 6A, the maximum luminance angle $\theta_{max}$ with which the luminance value is maximum is an angle ($\theta_0 + \pi/4$) deviated from the phase component $\theta_0$ by 45°. With this configuration, it is, for example, possible to calculate the phase component $\theta_0$ at high S/N ratio. Also regarding other ROIs 75, a similar process is performed and is stored as the biological tissue information of the observation target 1.

Referring back to FIG. 9, when the anisotropic object 51 is identified, an emphasis image in which tissues different in optical anisotropy, a fibrous tissue direction (a direction of extension), and the like are emphasized is generated (Step 106). For example, an image showing the polarization property, the fibrous tissue direction, and the like for each ROI 75 is generated on the basis of the biological tissue information (the identification information, the phase component $\theta_0$, the amplitude Amp, and the like) calculated in Step 105.

Figure 13:
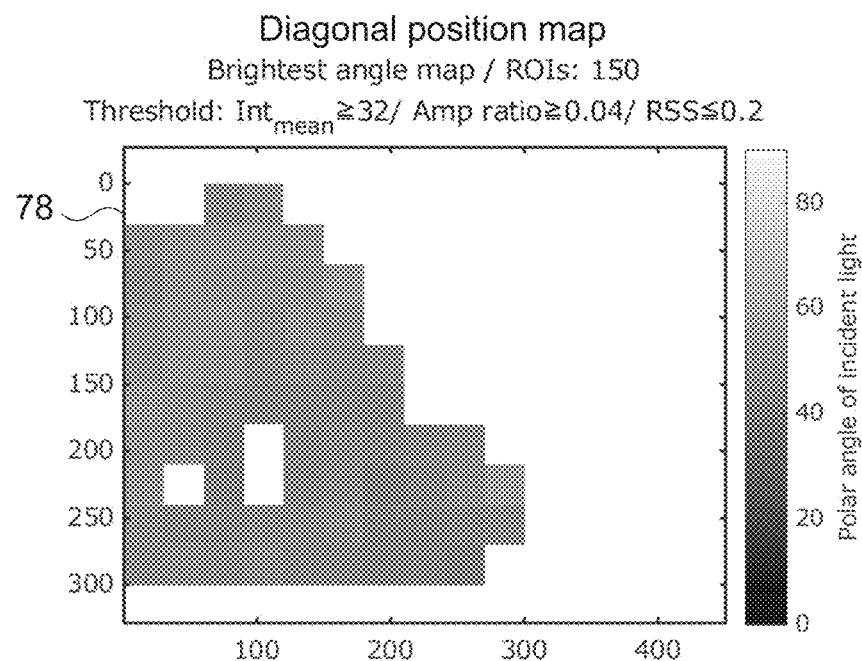
FIG. 13 A map image showing an example of an emphasis image.

FIG. 13 is a map image showing an example of the emphasis image. In the map image 78 shown in FIG. 13, the maximum luminance angle $\theta_{max}$ for each of ROIs determined to include the anisotropic object 51 is shown by using gradation display (hue display). The map image 78 is an emphasis image representing the polarization property of the anisotropic object 51. It should be noted that although the gradation is displayed in the gray scale in FIG. 13, the hue or the like in which arbitrary color is set is actually used as appropriate.

For example, it can be seen that the anisotropic object 51 exists in the regions in which the gradation color is displayed. It is identified that many ROIs 75 include the anisotropic object 51 in a site in which the muscle layer 84 is exposed as shown in FIG. 13. Meanwhile, it is identified that many ROIs 75 do not include the anisotropic object 51 in a site in which the mucosa 82 or the submucosa 83 is exposed. By referring to the map image 78 in this manner, It is possible to identify the muscle layer region and the mucosa region with high accuracy.

In addition, in the map image 78, the maximum luminance angle $\theta_{max}$ of each ROI 75 provided in the site in which the muscle layer 84 is exposed is a value close to 45°. Therefore, for example, in the region identified to include the anisotropic object 51, it is possible to estimate that the anisotropic object 51 is oriented in substantially uniform directions.

The parameter displayed as the map image 78 is not limited. The map image 78 representing the orientation, the anisotropy, and the like of the anisotropic object 51 for each ROI 75 may be generated on the basis of the amplitude Amp of the first intensity and the like calculated for each ROI 75, for example. Moreover, the map image 78 and the like representing the reliability of fitting in the ROI 75 may be generated by using the residual sum of squares and the like for each ROI 75.

Figure 14:
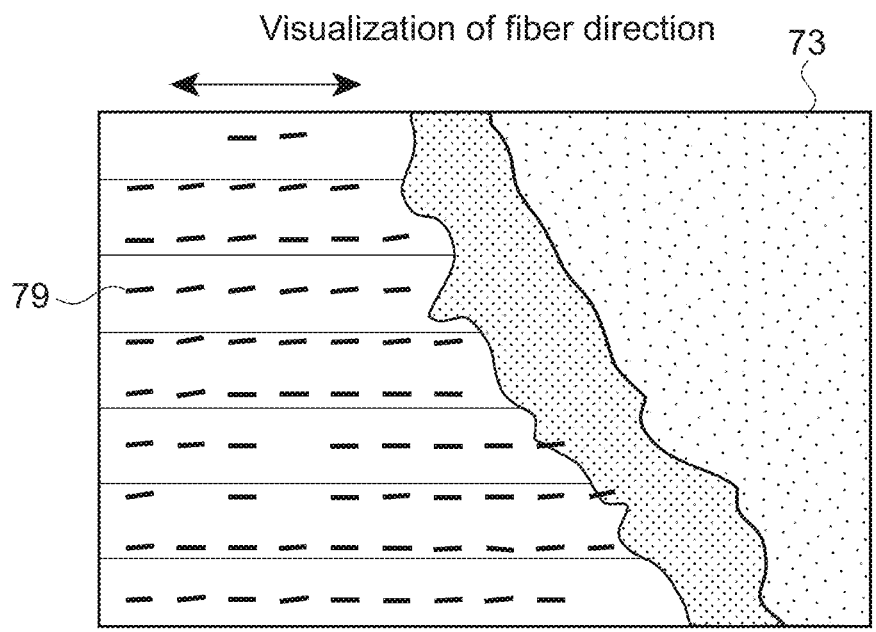
FIG. 14 An observation image showing another example of the emphasis image.

FIG. 14 is an observation image showing another example of the emphasis image. FIG. 14 schematically shows the observation image 73 observed in crossed nicols observation. Moreover, the fiber direction 54 calculated on the basis of the maximum luminance angle $\theta_{max}$ of the map image 78 shown in FIG. 13 for each ROI is shown as a thick line 79. As shown in FIG. 14, in the observation image 73, the fiber directions 54 of the muscle layer 84 are displayed in an emphasis state, overlapping the actually observed image.

The fiber direction 54 is expressed by, for example, an angle obtained by subtracting 45° from the maximum luminance angle $\theta_{max}$, i.e., the value of the phase component $\theta_0$. As shown in FIG. 14, the thick line 79 displayed in each ROI 75 is a direction substantially parallel to the left and right directions 71 of the observation image 73. That is, it can be said that the fiber directions 54 of the muscle layer 84 indicate directions similar to predicted directions (the arrows in the figure) of anatomical muscle fibers, which have been described with reference to FIG. 8. By performing crossed nicols observation using the microscope device 100 in this manner, it is possible to predict the directions of extension and the like of muscle fibers with high accuracy.

The generated emphasis images (the map image 78, the observation image 73, and the like) are output to the display unit 50 as intraoperative images. The intraoperative images are displayed on the display unit 50. With this configuration, for example, it is possible to easily determine whether or not the anisotropic object 51 is seen in a site that is a target of surgery or examination. Moreover, it is possible to specifically observe the orientation direction of the anisotropic object 51, a distribution of orientation directions, and the like.

As described above, in the microscope device 100 according to this embodiment, the plurality of polarization light beams 3 different in the polarization direction is sequentially emitted to the observation target 1. The reflection light beam 4 from the observation target 1 is incident upon the plurality of pixels 35 having the predetermined number of pixels as the one group while its polarization state is controlled. At this time, the mutually different polarization components 5 are incident upon respective ones of the predetermined number of pixels 35. Then, the biological tissue information regarding the observation target 1 from the pixel signals output from the respective ones of the predetermined number of pixels 35 is calculated. With this configuration, it is possible to sufficiently assist biological tissue observation.

A method using a Mueller imaging system capable of calculating a Mueller matrix is conceivable as a method of observing the biological tissue by emitting the polarization light beams. In the Mueller imaging system, the plurality of polarization light beams different in the polarization state are sequentially emitted to the object to be imaged and the polarization property corresponding to the anisotropic object (depolarization ratio, polarization degree of light, phase difference, direction of phase difference, direction of absorption, optical rotation) are obtained. For example, by combining and displaying two or more polarization property images on the basis of those polarization property, a doctor identifies an appearing tissue from a lesion part and diagnoses of the degree of invasion in the mucosa and the like.

In order to generate two or more polarization property images, a Mueller matrix of 4×4 is calculated in the method using the Mueller imaging system. In this case, it is necessary to obtain at least 16 images and perform analysis processing on those images, and it takes time to perform imaging and analysis processing and observation by a doctor in real time it can be difficult. Moreover, in capturing the 16 images, it can be difficult to suitably obtain the images due to body motion or pulsing of an object to be imaged, vibrations of the device or the environment, hand shaking of a person who performs imaging, and the like.

In addition, a method using a commercially available polarization camera and the like is conceivable as an observation method of detecting polarization components. In the commercially available polarization camera, polarization angles that can be detected are set in intervals of 45° (e.g., polarization transmission axes of four directions of 0°, 45°, 90°, and 135°) in some cases. For example, when observing an optically anisotropic object in crossed nicols observation, the observation light intensity becomes a function with a cycle of 90° and the same values can be detected at the intervals of 45°.

Therefore, in the polarization camera having polarization transmission axes at the intervals of 45°, the same values can be detected in all directions and accurate crossed nicols observation can be difficult. As a result, identification of fibrous tissues of a living organism, determination of directions of fibers, detection of tissue changes, and the like can be incapable of being appropriately performed.

In the microscope device 100 according to this embodiment, the four light sources 24 are made to sequentially emit light beams and the polarization light beams 3 of the mutually different polarization directions are sequentially emitted to the observation target 1 from the four types of lighting polarizers 25 corresponding to the respective light sources 24. The reflection light beams 4 of the respective polarization light beams 3 reflected by the observation target 1 are sequentially obtained by polarization sensors 39 (the light-receiving polarizers 37 and the pixels 35) corresponding to the respective polarization light beams 3.

With this configuration, it is possible to switch the respective polarization light beams 3 at high speed and emit them and it is possible to sufficiently shorten the time necessary for observation of the observation target 1. That is, imaging necessary to calculate biological tissue information and the like of the observation target 1 can be performed at high speed. As a result, proper observation can be realized even if body motion, pulsing, or the like of the living organism, vibrations of the device or hand shaking of a person who performs imaging, environment vibrations, or the like, for example, occurs.

Moreover, a setting is made such that the incident polarization angle θ of the polarization light beam 3 emitted to the observation target 1 and the transmission angle φ set to the polarization sensors 39 intersect with each other at about 90°. Therefore, in the microscope device 100, crossed nicols observation using four types of incident polarization angles θ is possible. With this configuration, it is possible to realize accurate crossed nicols observation substantially in real time. As a result, the identification property of the biological tissue is enhanced and it is possible to sufficiently assist diagnosis and the like by a doctor.

By using the result of observation (the emphasis image and the like) of crossed nicols observation, highly accurate identification of the fibrous tissue and the non-fibrous tissue is performed substantially in real time. With this configuration, for example, it is possible to rapidly detect an exposed site during surgery also if a muscle layer is exposed due to undesired perforation or the like in resection or the like of a mucosa lesion of a digestive organ.

In addition, in this embodiment, the polarization transmission axis 38 with a pitch of 22.5° is set to the polarization camera 32. That is, crossed nicols observation in which the incident polarization angle θ is changed with a pitch of 22.5° is possible. With this configuration, four data points are obtained in a range of from 0° to 90°. As a result, it is possible to appropriately calculate a periodic function of 90° representing a change in the first intensity and identification of the fibrous tissue of the anisotropic object 51, determination of directions of fibers, detection of tissue changes, and the like can be realized with high accuracy.

For example, by analyzing information regarding the orientation of the anisotropic object 51 and mapping the orientation, the anisotropy, or the like, it is possible to display, in an emphasis state, a site where degradation of muscle fibers inside muscle, an abnormality of orientation of cardiac muscle cells in hypertrophic cardiomyopathy, degradation of collagen fibers that constitute a meniscus, or the like has occurred. As a result, it is possible to enhance the identification property of normal tissues and lesion tissues and it is possible to sufficiently assist biological tissue observation.

Second Embodiment

An endoscopic device 200 according to a second embodiment of the present technology will be described. In the following descriptions, descriptions of portions similar to the configurations and actions in the microscope device 100 described in the embodiment above will be omitted or simplified.

Figure 15:
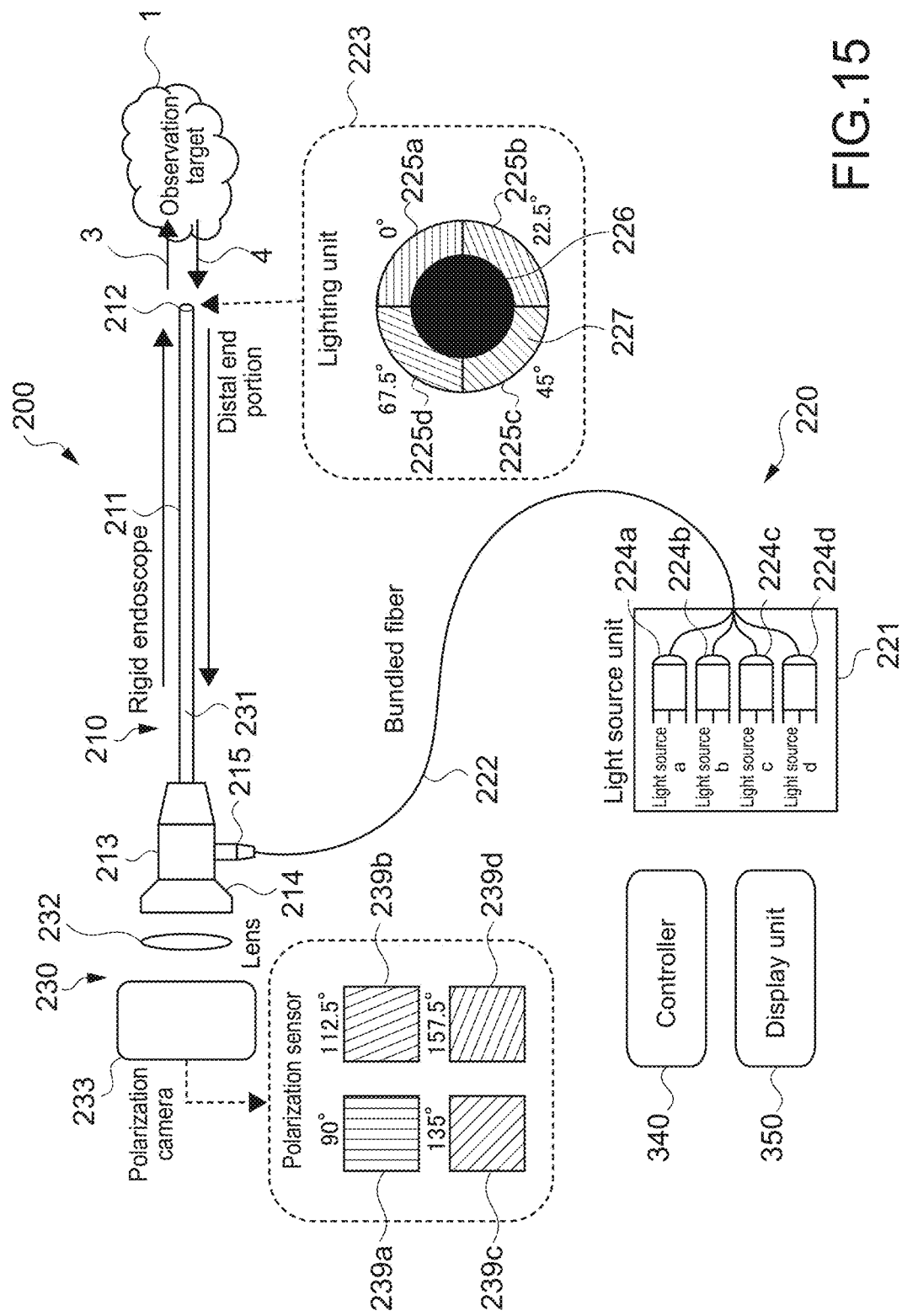
FIG. 15 A diagram schematically showing a configuration example of an endoscopic device which is an observation device according to a second embodiment of the present technology.

FIG. 15 is a diagram schematically showing a configuration example of an endoscopic device 200 which is an observation device according to a second embodiment of the present technology. The endoscopic device 200 includes an insertion unit 210, a lighting system 220, an imaging system 230, a controller 240, and a display unit 250. The endoscopic device 200 is configured as a rigid endoscope used for observation and the like in laparoscopy or otorhinolaryngological fields. It should be noted that the controller 240 and the display unit 250 shown in FIG. 15 are configured to in a way similar to that of the controller 40 and the display unit 50 shown in FIG. 1.

The insertion unit 210 includes a rigid portion 211, a distal end portion 212, and an operation unit 213. The rigid portion 211 has a thin tubular structure and is constituted by a rigid material such as stainless steel. The material, size, and the like of the rigid portion 211 are not limited, and may be set as appropriate depending on purposes such as surgery and observation purposes.

The distal end portion 212 is provided at one end of the rigid portion 211. The distal end portion 212 is inserted into a vicinity of the observation target 1 through a hole or the like opened in the abdominal region of a patient. The distal end portion 212 is provided with a lighting unit 223 to be described later. In addition to this, the distal end portion 212 may be provided with a nozzle that is an outlet for water, the air, or the like, a treatment tool outlet through which forceps or the like are inserted and removed, and the like as appropriate.

The operation unit 213 is provided at an end of the rigid portion 211 opposite to the distal end portion 212. The operation unit 213 includes a scope holder 214 and an optical port 215. A forceps port or the like through which a treatment tool such as forceps is inserted and removed, for example, may be used as a light port 215. In addition to this, the operation unit 213 may be provided with a lever, a switch, or the like necessary for operation and the like of the insertion unit 210 as appropriate.

The lighting system 220 includes a light source unit 221, bundled fibers 222, and the lighting unit 223. The light source unit 221 has a configuration similar to that of the light source unit 21 shown in FIG. 1. The bundled fibers 222 are a bundle of a plurality of optical fibers. The bundled fibers 222 include a plurality of fiber bundles each constituted by a bundle of optical fibers.

One end of each fiber bundle is connected to each of light sources 224a to 224d. The fiber bundles connected to the respective light sources 224a to 224d are grouped together as a single bundle, are introduced into the light port 215, passes through the inside of the rigid portion 211, and are placed to the distal end portion 212. Therefore, emission light beams emitted from the respective light sources 224a to 224d are respectively individually transmitted through the fiber bundles.

The lighting unit 223 is provided at the distal end portion 212. FIG. 15 schematically shows a configuration example of the lighting unit 223. The lighting unit 223 has a circular plate shape and includes an aperture 226 and lighting polarizers 225a to 225d. The aperture 226 is arranged at the center of the lighting unit 223 and functions as an observation window through which the reflection light beam 4 from the observation target 1 or the like passes.

The lighting polarizers 225a to 225d include respective emission surfaces 227. The respective emission surfaces 227 has a shape obtained by dividing a region surrounded by an inner circle and an outer circle having a common center into four parts by a straight line passing through the center. The lighting polarizers 225a to 225d are respectively arranged to surround the aperture 226 with the emission surfaces 227 directed to the observation target 1. It should be noted that emission light beams from the light sources 224a to 224d are respectively incident upon surfaces opposite to the emission surfaces 227 of the respective lighting polarizers 225a to 225d.

Mutually different incident polarization axes 229 are respectively set to the lighting polarizers 225a to 225d. In this embodiment, a direction parallel to the incident polarization axis 229 of the lighting polarizer 225a is set as the reference direction 60. The lighting polarizer 225b has the incident polarization axis 229 rotated by about 22.5° in the direction of left rotation from the reference direction 60. The lighting polarizer 225c has the incident polarization axis 229 rotated by about 45° in the direction of left rotation from the reference direction 60. The lighting polarizer 225d has the incident polarization axis 229 rotated by about 67.5° in the direction of left rotation from the reference direction 60. Therefore, the lighting polarizers 225a to 225d respectively emit the polarization light beams 3 having the incident polarization angle $\theta$=0°, 22.5°, 45°, and 67.5°.

It should be noted that a specific configuration of the lighting unit 223 is not limited. For example, a configuration in which eight types of polarization light beams 3 are emitted may be used by dividing the lighting unit 220 into eight. Moreover, a configuration in which a non-polarization light beam is emitted from the lighting unit 223 may be employed.

The imaging system 230 includes a relay optical system 231, a lens unit 232, and a polarization camera 233. The relay optical system 231 is an optical system that establish connection from the aperture 226 of the lighting unit 220 to the scope holder 214 and is provided inside the insertion unit 210. The relay optical system 231 is configured as appropriate to be capable of retaining the polarization direction of the reflection light beam 4. As shown in FIG. 15, the reflection light beam 4 reflected by the observation target 1 is emitted passing through the relay optical system 231 arranged inside the insertion unit 210.

The lens unit 232 is arranged outside the scope holder 214, enlarges or reduces the reflection light beam 4 emitted from the scope holder 214 as appropriate, and causes the reflection light beam 4 to be incident upon the polarization camera 233.

The polarization camera 233 has a configuration similar to that of the polarization camera 32 shown in FIG. 1, for example. That is, the polarization camera 233 includes polarization sensors 239a to 239d having the transmission angle $\varphi$=90°, 112.5°, 135°, and 157.5° and functions as a polarization image sensor in which the polarization sensors 239a to 239d are arranged as one group.

As in the first embodiment, in the endoscopic device 200, the light sources 224a to 224d are made to sequentially emit light beams and the polarization light beams 3 having the incident polarization angle $\varphi$=0°, 22.5°, 45°, and 67.5° are respectively emitted. Moreover, the polarization sensors 239a to 239b having the transmission angle $\Psi$ orthogonal to the respective polarization light beams 3 sequentially perform imaging processing of the observation target 1 (see FIGS. 9, 10A, and 10B). On the basis of four pieces of image data obtained in the imaging processing, the biological tissue information is calculated, the emphasis image representing the fiber directions, the orientation, the anisotropy, and the like of the anisotropic object included in the observation target 1 is displayed on the display unit 250.

As described above, even with the endoscopic device 200 configured as the rigid endoscope, it is possible to perform crossed nicols observation at high speed and it is possible to observe the biological tissue substantially in real time with high accuracy. With this configuration, it is possible to sufficiently assist biological tissue observation also in observation or the like in laparoscopy or otorhinolaryngological fields.

Third Embodiment

Figure 16:
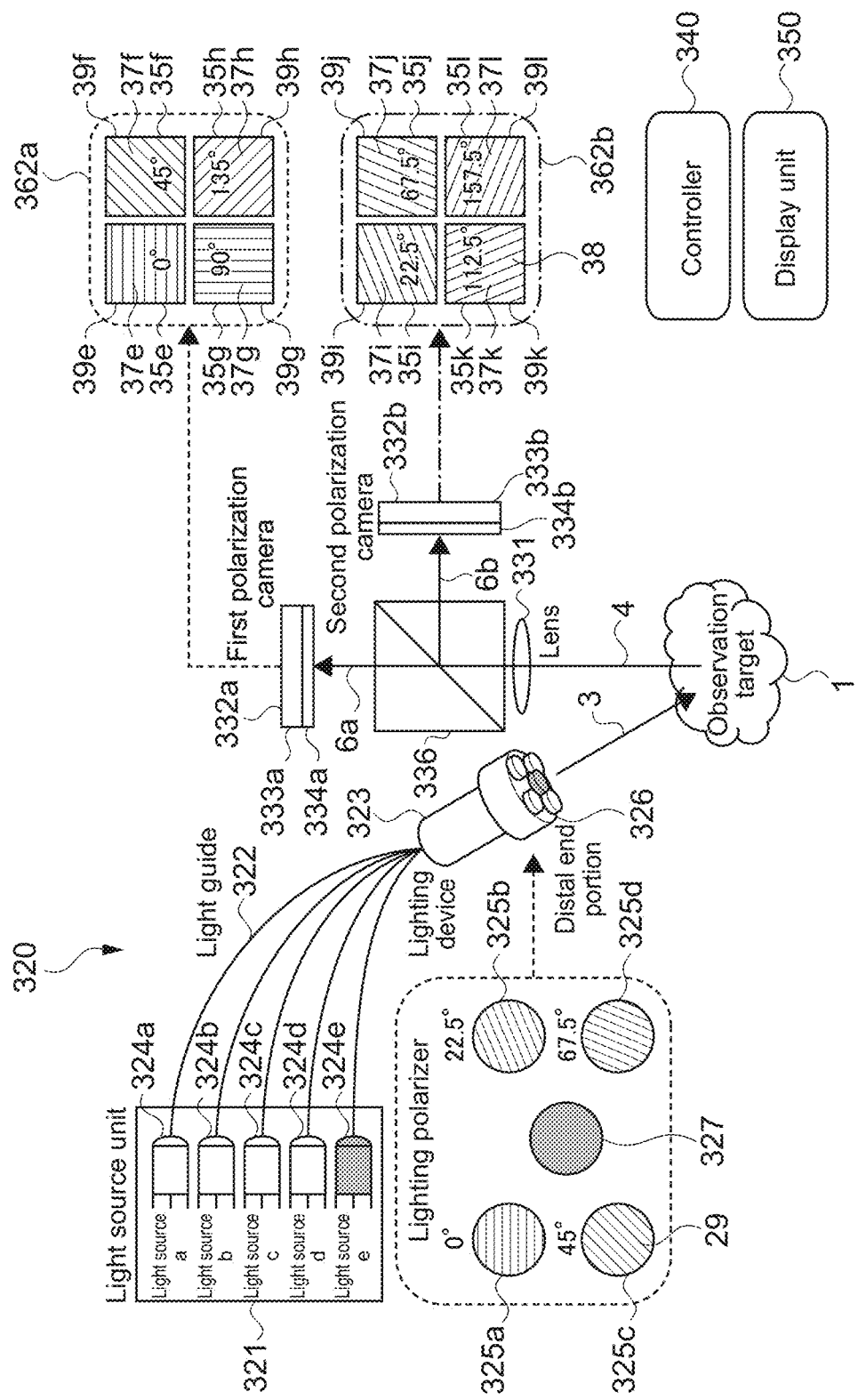
FIG. 16 A diagram schematically showing a configuration example of a microscope device which is an observation device according to a third embodiment of the present technology.

FIG. 16 is a diagram schematically showing a configuration example of a microscope device 300 which is an observation device according to a third embodiment of the present technology. In this embodiment, the microscope device 300 performs observation (open nicol observation) of the observation target 1 in an open nicol in addition to crossed nicols observation.

The microscope device 300 includes a lighting system 320, an imaging system 330, a controller 340, and a display unit 350. The display unit 350 is configured in a way similar to that of the display unit 350 shown in FIG. 1, for example.

The lighting system 320 includes a light source unit 321, a light guide 322, and a lighting device 323. The light source unit 321 includes five light sources 324a to 324e. Moreover, the light sources 324a to 324d each have a configuration similar to that of the light sources 24a to 24d described above with reference to FIG. 1, for example. The light source 324e emits an emission light beam that is a non-polarization light beam. A white light emitting diode (LED), a xenon lamp, or the like is used as the light source 324e. Emission light beams emitted from the five light sources 324a to 324e are individually transmitted through the light guide 322.

The lighting device 323 includes lighting polarizers 325a to 325d and a non-polarization light emission unit 327. FIG. 16 schematically shows a configuration example of the lighting polarizers 325a to 325d and the non-polarization light emission unit 327 which are provided at a distal end portion 326 of the lighting device 323. Moreover, the lighting device 323 is configured as appropriate such that emission light beams emitted from the light sources 324a to 324d are respectively incident upon the lighting polarizers 325a to 325d and the emission light beam emitted from the light source 324e is incident upon the non-polarization light emission unit 327.

Mutually different incident polarization axes 29 are respectively set to the lighting polarizers 325a to 325d. In this embodiment, a direction parallel to the incident polarization axis 29 of the lighting polarizer 325a is set as the reference direction 60. The lighting polarizer 325b includes the incident polarization axis 29 rotated by about 22.5° in the direction of left rotation from the reference direction 60. The lighting polarizer 325c includes the incident polarization axis 29 rotated by about 45° in the direction of left rotation from the reference direction 60. The lighting polarizer 325d includes the incident polarization axis 29 rotated by about 67.5° in the direction of left rotation from the reference direction 60. Therefore, the lighting polarizers 325a to 325d respectively emit polarization light beams having the incident polarization angle θ=0°, 22.5°, 45°, and 67.5°.

The non-polarization light emission unit 327 emits a non-polarization light beam emitted from the light source 324e while maintaining its polarization state. Therefore, a non-polarization light beam not having a particular polarization direction is emitted toward the observation target 1 from the non-polarization light emission unit 327. A glass plate, an acrylic plate, or the like, for example, is used as the non-polarization light emission unit 327. In addition to this, a diffusion plate that diffuses the non-polarization light beam, a lens, and the like may be used. As described above, the lighting system 320 is capable of emitting the non-polarization light beam to the observation target 1.

The imaging system 330 includes a lens unit 331, a separation optical system 336, a first polarization camera 332a, and a second polarization camera 332b. The lens unit 331 has a zoom function of enlarging and reducing the reflection light beam 4 from the observation target 1. The lens unit 331 is configured as appropriate such that imaging of the first and second polarization cameras 332a and 332b at the subsequent stage is capable of being appropriately performed, for example. The reflection light beam 4 that has passed through the lens unit 331 is incident upon the separation optical system 336.

The separation optical system 336 separates the reflection light beam 4 from the observation target 1 into a first separated light beam 6a and a second separated light beam 6b that travel in the mutually different directions. Typically, the first and second separated light beams 6a and 6b are separated to have intensity substantially similar each other. As a matter of course, the present technology is not limited thereto.

As shown in FIG. 16, the separation optical system 336 causes the first separated light beam 6a to be incident upon the first polarization camera 332a and causes the second separated light beam 6b to be incident upon the second polarization camera 332b. An optical element such as a mirror (half mirror) and a prism having semi-transparency, for example, is used as the separation optical system 336 as appropriate. In addition to this, a specific configuration of the separation optical system 336 is not limited.

The first polarization camera 332a includes a first image sensor 333a and a first polarization unit 334a. The first image sensor 333a includes a plurality of pixels 35. The plurality of pixels 35 is arrayed in two directions orthogonal to each other in the light-receiving surface of the first image sensor 333a (see FIG. 2). In this embodiment, the plurality of pixels 35 of the first image sensor 333a corresponds to first pixels.

The first polarization unit 334a includes a plurality of light-receiving polarizers 37. The plurality of light-receiving polarizers 37 each have a polarization transmission axis 38 (polarization axis) and are respectively arranged corresponding to the plurality of pixels 35 of the first image sensor 333a. Therefore, a plurality of polarization sensors 39 that is a pair of the light-receiving polarizer 37 and the pixel 35 is configured in the first polarization camera 332a.

In the first polarization unit 334a, the pixels 35 of the first image sensor 333a are divided into groups including the predetermined number of pixels 35. Then, a predetermined number of light-receiving polarizers 37 having mutually different polarization transmission axes 38 (the transmission angles φ) are arranged respectively corresponding to the predetermined number of pixels included in the one group 35. Hereinafter, the group set in the first image sensor 333a will be referred to as a first group 362a.

As shown in FIG. 16, the first group 362a includes four pixels 35e to 35h and four light-receiving polarizers 37e to 37h arranged corresponding to the respective pixels 35e to 35h. Two of the four pixels 35e to 35h are arrayed in each of the two directions orthogonal to each other. It should be noted that in this embodiment, the four light-receiving polarizers 37e to 37h correspond to a plurality of first polarization elements that is arranged corresponding to the predetermined number of the first pixels, the predetermined number of the first pixels being considered as a first group.

In the example shown in FIG. 16, the light-receiving polarizer 37e having the polarization transmission axis 38 substantially parallel to the reference direction 60 is arranged at the upper left of the first group 362a. Moreover, the light-receiving polarizer 37f having the polarization transmission axis 38 rotated by about 45° in the direction of left rotation from the reference direction 60 is arranged at the upper right. Moreover, the light-receiving polarizer 37g having the polarization transmission axis 38 rotated by about 90° in the direction of left rotation from the reference direction 60 is arranged at the lower left. Moreover, the light-receiving polarizer 37h having the polarization transmission axis 38 rotated by about 135° in the direction of left rotation from the reference direction 60 is arranged at the lower right.

As described above, in this embodiment, the first group 362a includes the polarization sensors 39e to 39h with a pitch of 45° having the transmission angles φ=0°, 45°, 90°, and 135°. Therefore, it is possible to use commercially available polarization image sensors or the like with a pitch of 45° as the first polarization camera 332a, for example. It should be noted that the array pattern and the like of the respective polarization sensors 39e to 39h are not limited. For example, an array pattern in which the array shown in FIG. 16 is repeated may be used. Moreover, those may be arrayed as appropriate on the basis of the array pattern and the like described above with reference to FIGS. 2 and 3, for example.

The second polarization camera 332b includes a second image sensor 333b and a second polarization unit 334b. The setting value of the transmission angle φ and the arrangement of the second polarization camera 332b are different from those of the first polarization camera 332a. The second image sensor 333b includes a plurality of pixels 35. The number of pixels (resolution) of the second image sensor 333b is set to be similar to the number of pixels of the first image sensor 333a. In this embodiment, the plurality of pixels 35 of the second image sensor 333b corresponds to second pixels.

A second polarization unit 324b includes a plurality of light-receiving polarizers 37. In the second polarization unit 324b, the pixels 35 of the second image sensor 333b are divided into a second group 362b including a predetermined number of pixels 35 and the predetermined number of light-receiving polarizers 37 are arranged respectively corresponding to the predetermined number of pixels 35.

As shown in FIG. 16, the second group 362b includes four pixels 35i to 35l and four light-receiving polarizers 37i to 37l arranged corresponding to the respective pixels 35i to 35l. It should be noted that in this embodiment, the four light-receiving polarizers 37i to 37l correspond to a plurality of second polarization elements that is arranged corresponding to the predetermined number of the second pixels, the predetermined number of the second pixels being considered as a second group.

In the example shown in FIG. 16, the light-receiving polarizer 37l having the polarization transmission axis 38 rotated by about 22.5° in the direction of left rotation from the reference direction 60 is arranged at the upper left of the second group 362b. Moreover, the light-receiving polarizer 37j having the polarization transmission axis 38 rotated by about 67.5° in the direction of left rotation from the reference direction 60 is arranged at the upper right. Moreover, the light-receiving polarizer 37k having the polarization transmission axis 38 rotated by about 112.5° in the direction of left rotation from the reference direction 60 is arranged at the lower left. Moreover, the light-receiving polarizer 37l having the polarization transmission axis 38 rotated by about 157.5° in the direction of left rotation from the reference direction 60 is arranged at the lower right.

As described above, in this embodiment, the second group 362b includes the polarization sensors 39i to 39l with a pitch of 45° having the transmission angles $\varphi$=22.5°, 67.5°, 112.5°, and 157.5°. It should be noted that the transmission angles T set to the polarization sensors 39i to 39l are values obtained by rotating the transmission angles T set to the polarization sensors 39e to 39h of the first polarization camera 332a by 22.5° in the direction of left rotation.

The first polarization camera 332a and the second polarization camera 332b are connected to the controller 340 and are controlled as appropriate to perform imaging of the observation target 1 in accordance with the timings of light emission of the light source unit 321. The output data (the pixel signals) output from the respective polarization cameras is output to the controller 340 and is used for calculating biological tissue information and the like of the observation target 1.

Figure 17A:
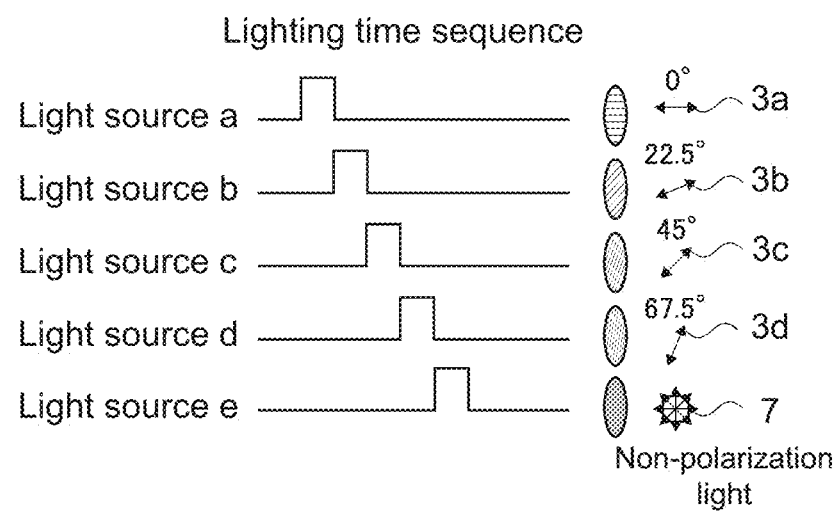
FIGS. 17A and 17B Schematic views showing an example of a time sequence of biological tissue observation.
Figure 17B:
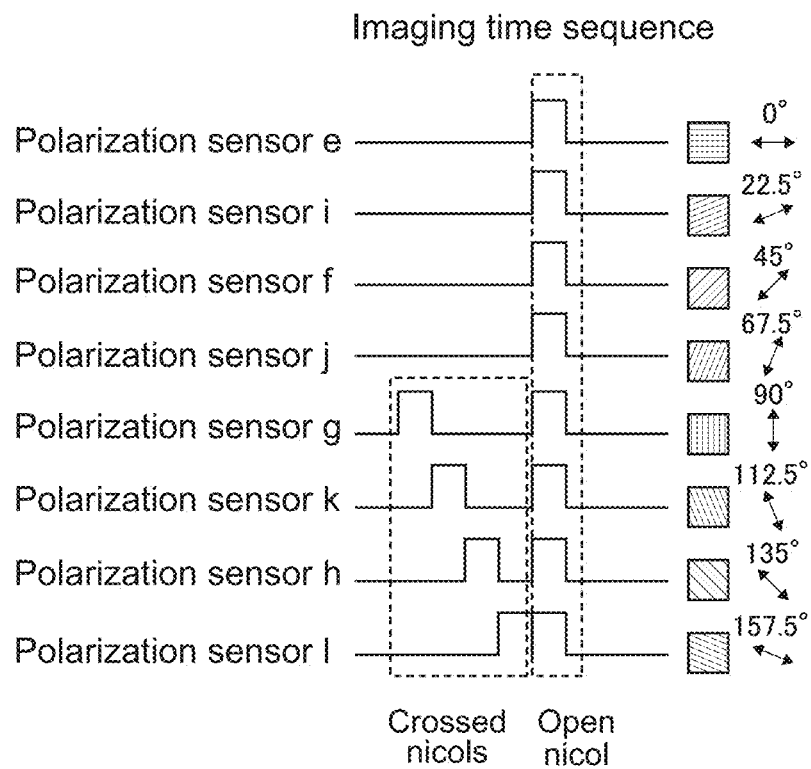

FIGS. 17A and 17B are schematic views showing an example of a time sequence of biological tissue observation. FIG. 17A is a schematic view showing a lighting time sequence representing timings of light emission of the respective light sources 324a to 324e. FIG. 17B is a schematic view showing a time sequence of imaging representing timings of imaging.

As shown in FIG. 17A, in this embodiment, the light source 324a to the light source 324e are made to sequentially emit light beams in the stated order. Therefore, the polarization light beams 3a to 3d having the incident polarization angle θ of 0°, 22.5°, 45°, and 67.5° are sequentially emitted to the observation target 1 and a non-polarization light beam 7 is emitted thereafter.

In synchronization with the emission periods of the polarization light beams 3a to 4d, the controller 340 performs imaging processing by using the polarization sensors 39 having the transmission angles $\varphi$ orthogonal to the incident polarization angles θ of the respective polarization light beams 3a to 4d. That is, crossed nicols observation to detect the polarization component 5 orthogonal to each of the polarization light beams 3a to 4d emitted to the observation target 1 is sequentially performed.

As shown in FIG. 17B, a pixel signal of the polarization sensor 39g having the transmission angle 90° is obtained from the first polarization camera 332a in accordance with the emission period of the polarization light beam 3a having the incident polarization angle 0°. A pixel signal of the polarization sensor 39k having the transmission angle 112.5° is obtained from the second polarization camera 332b in accordance with the emission period of the polarization light beam 3b having the incident polarization angle of 22.5°. A pixel signal of the polarization sensor 39h having the transmission angle 135° is obtained from the first polarization camera 332a in accordance with the emission period of the polarization light beam 3c having the incident polarization angle of 45°. A pixel signal of the polarization sensor 39l having the transmission angle 157.5° is obtained from the second polarization camera 332b in accordance with the emission period of the polarization light beam 3d having the incident polarization angle of 67.5°.

As described above, in this embodiment, crossed nicols observation is performed by using the polarization sensors 39 respectively provided in the first polarization camera 332a and the second polarization camera 332b. Moreover, four crossed nicols images (image data) are generated on the basis of the pixel signals sequentially obtained by using the polarization sensors 39g, 39k, 39h, and 39l.

In addition, in this embodiment, in a case where the non-polarization light beam 7 is emitted, the plurality of pixel signals output from the pixels 35e to 35l included in the first and second groups 362a and 362b is obtained. That is, imaging processing using all the polarization sensors 39 of the first polarization camera 332a and the second polarization camera 332b is performed in synchronization with the emission period of the non-polarization light beam 7.

With this configuration, eight types of polarization components different in the transmission angle T included in the reflection light beam 4 from the observation target 1 to which the non-polarization light beam 7 has been emitted are detected at the same time. Then, eight pieces of image data are generated on the basis of the pixel signals respectively output from eight types of polarization sensors 39 (the polarization sensors 39e to 39h and the polarization sensors 39i to 39l).

As described above, in this embodiment, open nicol observation to emit the non-polarization light beam 7 to the observation target 1 and detect the polarization components (the straight polarization light beam) included in the reflection light beam 4 from the observation target 1 is realized.

The open nicol observation is observation performed by inserting a polarizer at one position on an observation optical path on which the non-polarization light beam is emitted and the reflection light beam from the observation target is detected, for example. Hereinafter, the polarizer inserted into the observation optical path will be referred to as a detection polarizer. In the microscope device 300, the light-receiving polarizer 37 functions as the detection polarizer. It should be noted that open nicol observation in which the lighting polarizer 325 is used as the detection polarizer can be employed. This point will be described in a fourth embodiment.

Detection light intensity detected when the anisotropic object 51 is observed by open nicol observation is provided by the following equation by using a detection polarization angle ω of the detection polarizer.

$$\alpha * \cos^2(\omega - \theta_0) \tag{2}$$

Where α indicates the amplitude and is a constant depending on optical anisotropy (birefringence and the like) of the anisotropic object 51, for example. $\theta_0$ indicates a phase component and corresponds to the fiber direction 54 of the anisotropic object 51. Moreover, in this embodiment, the detection polarization angle ω is the transmission angle φ of the light-receiving polarizer 37. Therefore, the second intensity changes in proportion to $\cos^2(\varphi - \theta_0)$ and is a periodic function that fluctuates with a cycle of $\pi$ (180°) with respect to the transmission angle φ.

As described above, the second intensity detected when the anisotropic object 51 is subjected to open nicol observation, it vibrates in a vibration cycle different from that of the first intensity detected in crossed nicols observation. By utilizing this difference in vibration cycle, a determination process of determining in which direction the fiber direction 54 of the anisotropic object 51 is oriented is performed. Hereinafter, the determination process of the fiber direction 54 of the anisotropic object 51 will be described specifically.

Figure 18A:
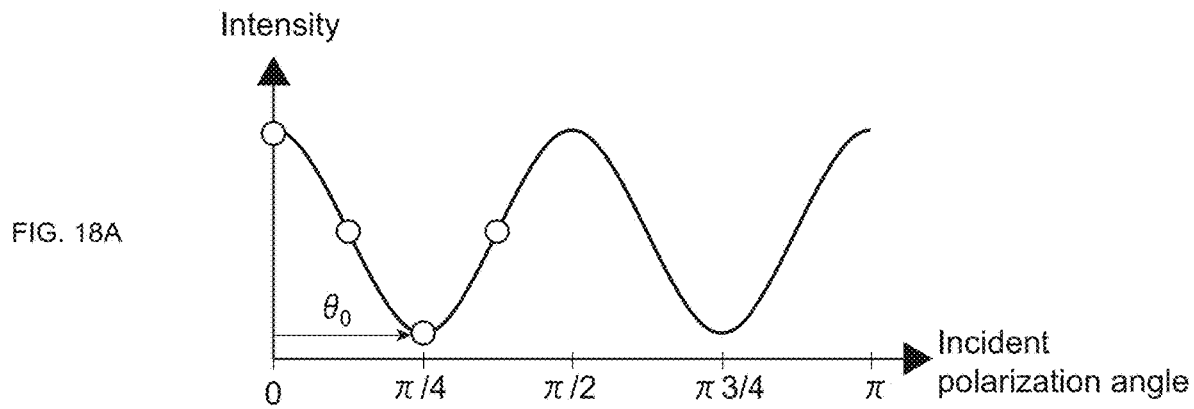
FIGS. 18A and 18B Graphs showing an example of changes in first intensity and second intensity.
Figure 18B:
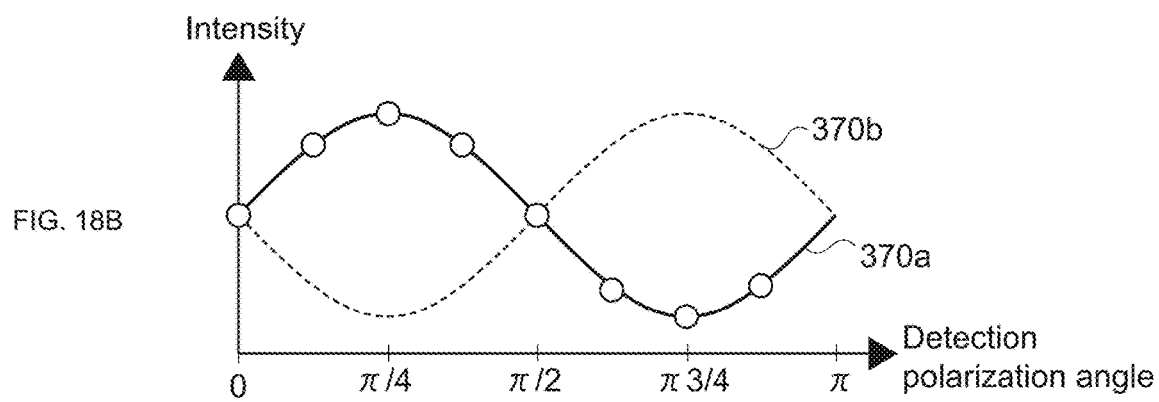

FIGS. 18A and 18B are graphs showing an example of changes in first intensity and second intensity. FIG. 18A is a graph showing a data point of the first intensity detected in crossed nicols observation. The horizontal axis and the vertical axis of the graph indicate the incident polarization angle and the first intensity.

For example, on the basis of the four pieces of image data obtained from crossed nicols observation, four data points representing the first intensity data is calculated for each ROI 75 (see FIG. 11). With respect to the calculated respective data points, the predetermined function f(θ) in the cycle of 90° is fitted. The amplitude of the first intensity data, the phase component $θ_0$, and the like are calculated on the basis of this fitting result.

As shown in the graph of FIG. 18A, the first intensity takes a minimum value with the incident polarization angle θ=45°. As described above, it is in a case where the polarization direction of the polarization light beam 3 and the fiber direction 54 of the anisotropic object 51 are parallel or orthogonal to each other that the first intensity is minimum. Therefore, the direction parallel or orthogonal to the incident polarization angle of 45° is the fiber direction.

Figure 19:
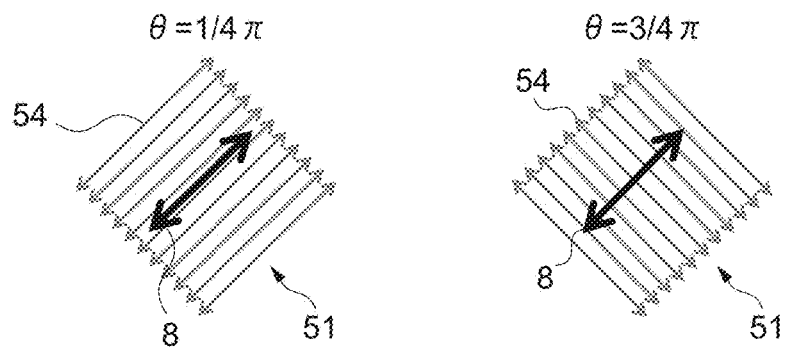
FIG. 19 A schematic view showing a relationship between a polarization direction of a polarization light beam and fiber directions of an anisotropic object.

FIG. 19 is a schematic view showing a relationship between the polarization direction of the polarization light beam 3 and the fiber direction 54 of the anisotropic object 51. FIG. 19 shows two types of fiber directions 54 estimated on the basis of the graph of FIG. 18A.

In the left picture of FIG. 19, the polarization direction 8 of the polarization light beam 3 of the incident polarization angle of 45° and the fiber direction 54 of the anisotropic object 51 are substantially parallel to each other. In this case, the fiber direction 54 is the direction rotated by about 45° (π/4) in the direction of left rotation from the reference direction 60 (the left and right directions of the observation image). In the right picture of FIG. 19, the polarization direction of the polarization light beam 3 having the incident polarization angle of 45° and the fiber direction 54 of the anisotropic object 51 are substantially orthogonal to each other. In this case, the fiber direction 54 the direction rotated by about 135° (3π/4) in the direction of left rotation from the reference direction 60.

FIG. 18B is a graph showing a data point of the second intensity that has been detected in open nicol observation. The horizontal axis and the vertical axis of the graph indicate the detection polarization angle ω (transmission angle φ) and the second intensity. It should be noted that the transmission angle φ indicates a rotational angle when rotating the reference direction 60 in the direction of left rotation as in the incident polarization angle θ. Therefore, the horizontal axis of the graph of FIG. 18A or 18B indicates a common angle.

For example, eight data points representing the second intensity data is calculated for each ROI 75 on the basis of eight pieces of image data obtained from open nicol observation. It should be noted that the method of calculating the data point (the mean luminance in the ROI 75) for each ROI is similar to a method of calculating the data point in crossed nicols observation.

With respect to the respective data points shown in FIG. 18B, the function with a cycle of 180° proportional to $\cos^2(φ-θ_0)$ on the basis of Equation (2) is fitted. FIG. 18B shows a fitting curve 370a indicating the fitted function as the solid line. This fitting curve 370a is maximum with a detection polarization angle of 45° (π/4). Therefore, the fitting curve 370a indicates a change in the second intensity in a case where the angle (the phase component $θ_0$) of the reference direction 60 and the fiber direction 54 is 45° (on the left side of FIG. 19).

It should be noted that FIG. 18B shows a fitting curve 370b indicating a function different from the fitting curve 370a as the solid line by the phase of 90° as the dotted line. The fitting curve 370b indicates a change in the second intensity in a case where the angle of the reference direction 60 and the fiber direction 54 is 135° (on the right side of FIG. 19).

As shown in FIG. 18B, the second intensity is a function in the cycle of 180°, and thus the fitting curves 370a and 370b whose phases are different by 90° do not overlap each other. Therefore, by referring to a change in the second intensity, it is possible to determine the actually observed fiber direction 54 of the two types of fiber directions 54 estimated on the basis of the change in the first intensity (graph of FIG. 18A).

As the determination process, for example, whether the graph of the second intensity protrudes upward or protrudes downward is determined in the first angle (the phase component $θ_0$) with which the first intensity is minimum when increasing the incident polarization angle θ from 0°. In a case where the graph of the second intensity protrudes upward, the direction parallel to the phase component $θ_0$ is the fiber direction 54. In the graph of the second intensity protrudes downward, the direction orthogonal to the phase component $θ_0$ is the fiber direction 54. For example, such a determination process is performed.

A specific method and the like of the determination process are not limited. For example, the fiber direction 54 may be determined by the threshold process using the average value of and the like of the data points of the second intensity. Moreover, the fiber direction 54 may be determined on the basis of the phase and the like of the graph indicating a change in the second intensity. In addition to this, an arbitrary process capable of appropriately determining the fiber direction 54 may be performed.

The fiber direction 54 is calculated for each ROI 75 on the basis of the result of the determination process and the emphasis image and the like showing the fiber direction 54 is generated as appropriate. With this configuration, it is possible to sufficiently specifically observe the direction of extension and the like of the fiber in addition to identification of the fibrous tissue 52 included in the observation target 1, for example.

As described above, in this embodiment, crossed nicols observation and open nicol observation are performed substantially in real time by sequentially emitting the plurality of polarization light beams 3 and the non-polarization light beam 7 from the lighting system 320. With this configuration, it is possible to display the emphasis image and the like showing a proper fiber direction 54 substantially in real time and it is possible to sufficiently assist biological tissue observation.

In addition, the first and second polarization cameras 332a and 332b are provided with the polarization sensors 39 having the eight types of transmission angles φ with a pitch of 22.5°. Four data points for crossed nicols and eight data points for open nicol can be obtained by using those polarization sensors 39. Therefore, data points for a single cycle can be obtained in either of crossed nicols and open nicol.

As a result, it is possible to accurately observe the fiber direction of the anisotropic object 51 and its boundary substantially in real time, and thus it is possible to observe the directions of muscle fibers that constitute muscle or the like, for example, during surgery.

Fourth Embodiment

Figure 20:
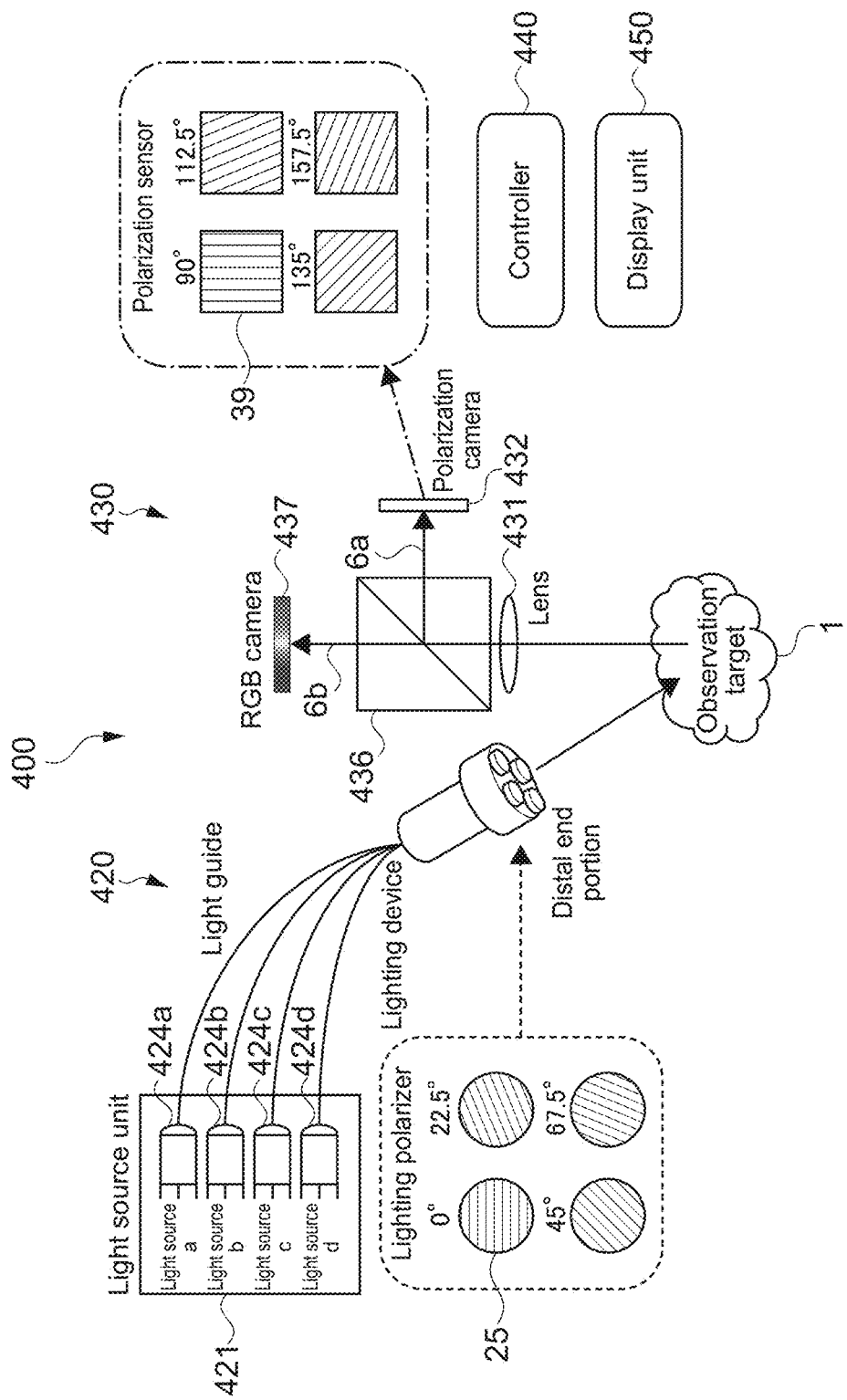
FIG. 20 A diagram schematically showing a configuration example of a microscope device which is an observation device according to a fourth embodiment of the present technology.

FIG. 20 is a diagram schematically showing a configuration example of a microscope device 400 which is an observation device according to a fourth embodiment of the present technology.

The microscope device 400 includes a lighting system 420, an imaging system 430, a controller 440, and a display unit 450. The lighting system 420 and the display unit 450 are configured to in a way similar to that of the lighting system 20 and the display unit 50 shown in FIG. 1.

The imaging system 430 includes a lens unit 431, a separation optical system 436, a polarization camera 432, and an RGB camera 437. The lens unit 431 and the separation optical system 436 are configured to in a way similar to that of the lens unit 431 and the separation optical system 436 shown in FIG. 16. The polarization camera 432 receives first separated light beam 6a emitted from the separation optical system 436. The polarization camera 432 has a configuration similar to that of the polarization camera 432 shown in FIG. 1.

The RGB camera 437 images the observation target 1 by receiving the second separated light beam 6b separated by the separation optical system 436. Moreover, pixel signals for constituting a color image of the observation target 1 are output from the plurality of pixels provided in the RGB camera 437. It should be noted that the RGB camera 437 is not provided with the light-receiving polarizer and the like. Therefore, the RGB camera 437 is capable of detection while maintaining the polarization state of the second separated light beam.

It should be noted that the number of pixels (resolution) of the RGB camera 437 is set to be similar to the number of pixels of the polarization camera 432, for example. A specific configuration of the RGB camera 437 is not limited, and a camera device including an image sensor such as a complementary metal-oxide semiconductor (CMOS) sensor and a charge coupled device (CCD) sensor, for example, may be used as appropriate. In this embodiment, the RGB camera 437 functions as the second image sensor.

Figure 21A:
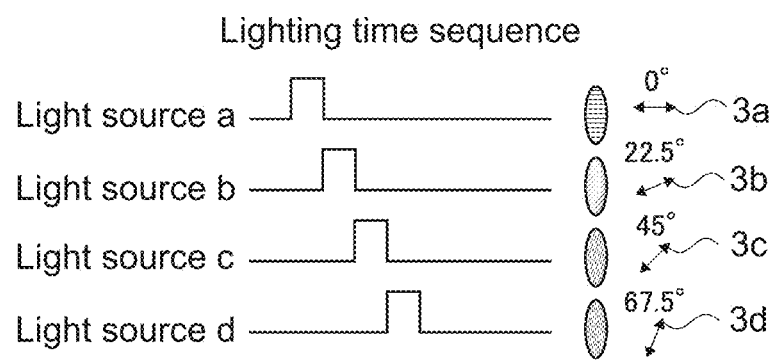
FIGS. 21A and 21B Schematic views showing an example of a time sequence of biological tissue observation.
Figure 21B:
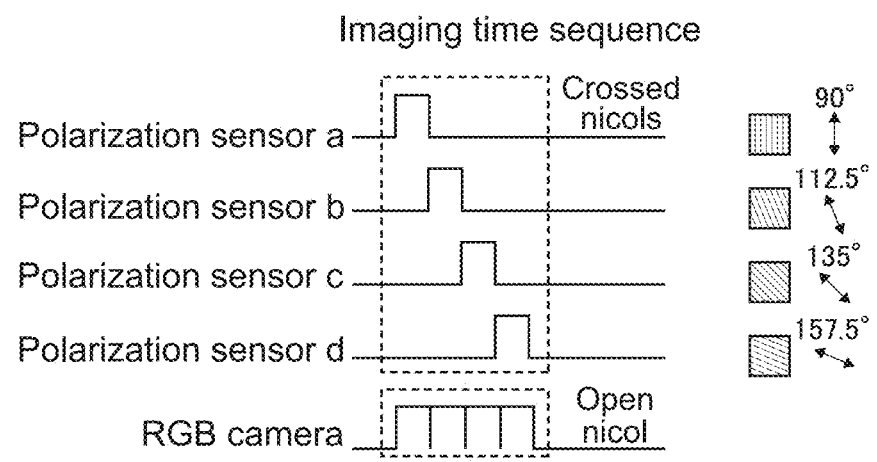

FIGS. 21A and 21B are schematic views showing an example of a time sequence of biological tissue observation. FIG. 21A is a schematic view showing a lighting time sequence representing timings of light emission of the respective light sources 24a to 24d. FIG. 21B is a schematic view showing a time sequence of imaging representing timings of imaging.

As shown in FIG. 21A, in this embodiment, light sources 424a to 424d are made to sequentially emit light beams in the stated order. Therefore, the polarization light beams 3a to 3d whose incident polarization angles θ are 0°, 22.5°, 45°, and 67.5° are sequentially emitted to the observation target 1.

As shown in FIG. 21B, the imaging processing is performed using the polarization sensors 39 having the transmission angles T orthogonal to the incident polarization angles θ of the respective polarization light beams 3a to 3d in synchronization with the emission periods of the polarization light beams 3a to 3d. That is, crossed nicols observation to detect the polarization component 5 respectively orthogonal to the polarization light beams 3a to 3d emitted to the observation target 1 is sequentially performed.

In addition, the RGB camera 437 respectively images the reflection light beams 4 from the observation target 1 when the respective polarization light beams 3 are reflected in synchronization with the emission periods of the polarization light beams 3a to 3d. The controller 440 generates color image data whose incident polarization angles θ are 0°, 22.5°, 45°, and 67.5° on the basis of the output data output in synchronization with emission of the respective polarization light beams 3a to 3d from the RGB camera 437.

As described above, imaging by the RGB camera 437 is open nicol observation to emit the non-polarization light beams (the emission light beams) to the observation target 1 from the light source via the lighting polarizer 25 and images its reflection light beam 4. Therefore, four pieces of color image data different in the incident polarization angle θ are open nicol images. It should be noted that in the microscope device 400, the lighting polarizer 25 functions as the detection polarizer and the incident polarization angle θ is the detection polarization angle ω.

Figure 22:
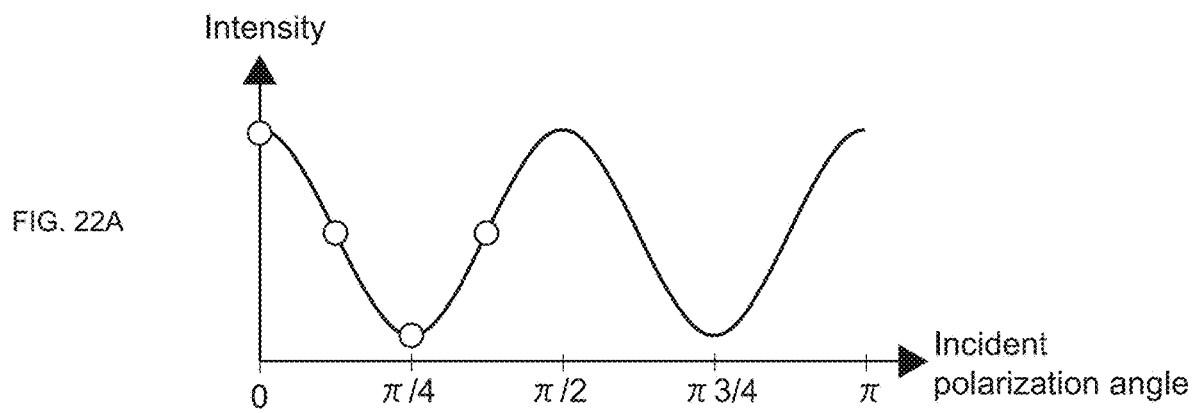
FIGS. 22A and 22B Graphs showing an example of changes in first intensity and second intensity.
Figure 22:
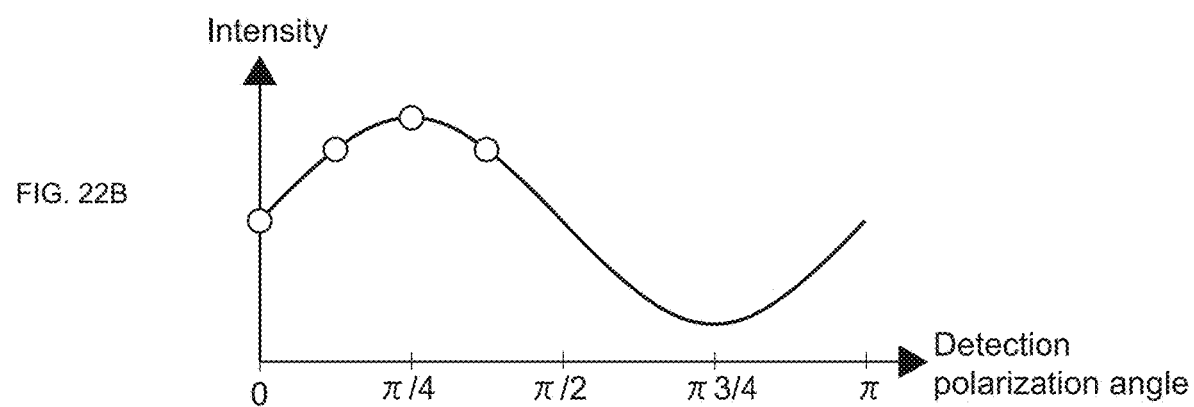

FIGS. 22A and 22B are graphs showing an example of changes in first intensity and second intensity. FIG. 22A is a graph showing data points of the first intensity detected in crossed nicols observation. FIG. 22B is a graph showing data points of the second intensity detected in open nicol observation.

As shown in FIGS. 22A and 22B, in this embodiment, four data points for crossed nicols observation are detected and four data points for open nicol observation are detected. It is possible to determine the fiber direction 54 or the like of the anisotropic object 51 (the fibrous tissue 52 and the like) included in the observation target 1 by performing the fitting process and the like on those data points as appropriate.

As described above, it is possible to realize crossed nicols observation and open nicol observation at the same time by separating the reflection light beam 4 from the observation target 1 and performing observation using both the polarization camera 432 and the RGB camera 437. It should be noted that the RGB camera 437 is provided with the polarization sensors 39 and the like, and thus it is possible to generate a high-resolution observation image. For example, the observation image 73 captured by using the RGB camera 437 is used for monitoring or the like of an operative field. With this configuration, it is possible to refer to a high-definition observation image.

It should be noted that in the configuration example shown in FIG. 20, the four types of polarization light beams 3 are generated whose incident polarization angles θ are 0°, 22.5°, 45°, and 67.5°. Not limited thereto, the light source and the lighting polarizer to emit the polarization light beam 3 in a wider angle range may be added. For example, it may be further possible to emit the polarization light beams 3 whose incident polarization angles θ are 112.5°, 157.5°, and the like in addition to the above-mentioned four types of polarization light beams.

As described above, by increasing the number of polarization light beams 3 and that can be emitted and the range, it is, for example, possible to increase the data points with respect to the second intensity detected in open nicol observation, i.e., the data points with respect to the second intensity that fluctuates with a cycle of 180° (see FIG. 22B). As a result, for example, it is possible to perform determination and the like of the fiber direction 54 with sufficiently high accuracy.

Moreover, although the RGB camera 437 is used in FIG. 20, an imaging device such as another camera can also be used. For example, it is possible to separate visible light and near-infrared light by using the dichroic mirror in the separation optical system. In this case, for example, a configuration in which the separated visible light is incident upon the polarization camera 432 and the near-infrared light is incident upon a near-infrared camera or the like may be used. With this configuration, it is possible to perform near-infrared analysis and the like in addition to polarization observation (crossed nicols observation and open nicol observation and the like). It is possible to sufficiently specifically observe the biological tissue.

Other Embodiments

The present technology is not limited to the above-mentioned embodiments and various other embodiments can be realized.

In the above-mentioned embodiment, emission light beams that are non-polarization light beams emitted from the plurality of light sources are transmitted to the lighting polarizers via the light guide, bundled fibers, and the like as the lighting system. Not limited thereto, an arbitrary configuration capable of emitting the plurality of polarization light beams may be used.

Figure 23A:
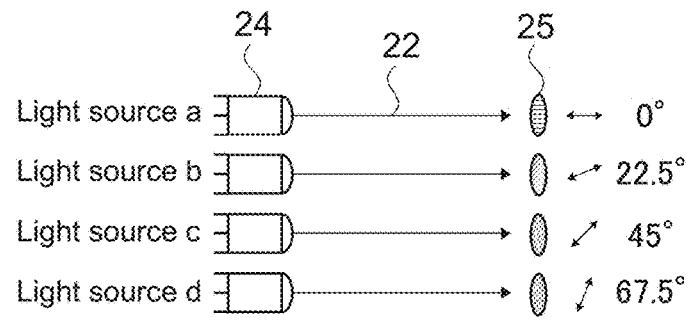
FIGS. 23A, 23B, 23C, and 23D Schematic views showing a configuration example of a lighting system.

FIGS. 23A, 23B, 23C, and 23D are schematic views showing a configuration example of the lighting system. FIG. 23A schematically shows a configuration of the lighting system described in the above-mentioned embodiment (e.g., FIG. 1 and the like). In FIG. 23A, emission light beams are respectively emitted from the plurality of light sources 24 and are made to pass through the light guide 22 (the optical fiber), and then straight polarization light beams are generated at the lighting polarizer 25. Therefore, it is unnecessary to retain the polarization directions and the like of the light beams that pass through the light guide 22. Therefore, it is possible to guide emission light beams at high efficiency without the need for using polarization retaining fibers and the like.

Figure 23B:
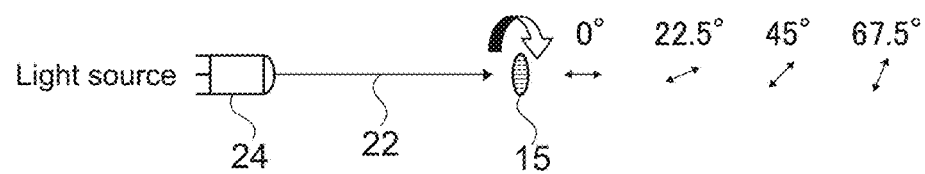

FIG. 23B shows a lighting system including a single light source 24 and a rotation polarization element 15 capable of rotating the polarization direction of a polarization light beam generated from an emission light beam of the light source 24. In this configuration, a non-polarization light beam emitted from the single light source 24 is emitted as the polarization light beam 3 by passing through the rotation polarization element 15. Moreover, the rotation polarization element 15 is capable of rotating the incident polarization angle θ (the polarization direction) of the polarization light beam 3 to be a predetermined angle such as 0°, 22.5°, 45°, or 67.5°. With this configuration, it is possible to reduce the number of light sources 24 and the number of polarizers, and it is possible to reduce the manufacturing cost and the like for the lighting system. Moreover, the number of components can be reduced, and thus the device size can be reduced.

Figure 23C:
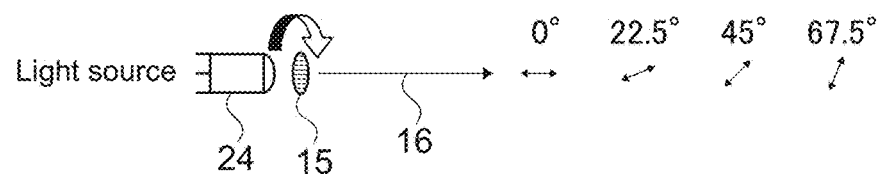

FIG. 23C shows a lighting system including a light source 24, a rotation polarization element 15, and a polarization retaining fiber 16. An LED light source or a xenon light source capable of emitting a non-polarization light beam, for example, is used as the light source 24. In this case, a polarization plate or the like that extracts a polarization light beam from a non-polarization light beam as the rotation polarization element 15 is used. Moreover, for example, a laser light source that emits a laser light beam may be used as the light source 24. In this case, a ½ plate or the like that rotates the polarization direction of the laser light beam is used as appropriate as the rotation polarization element 15.

In FIG. 23C, the emission light beam emitted from the light source 24 is incident upon the rotation polarization element 15 as it is. The polarization light beam output from the rotation polarization element is made to pass through the polarization retaining fiber 16 and is emitted to the observation target 1. With this configuration, for example, it is possible to reduce the size of configurations of the lighting device 23 shown in FIG. 1, the lighting unit 223 shown in FIG. 15, and the like. Therefore, for example, even with an endoscopic device having a thin distal end or the like, it is possible to appropriately emit a polarization light beam to the observation target.

Figure 23D:
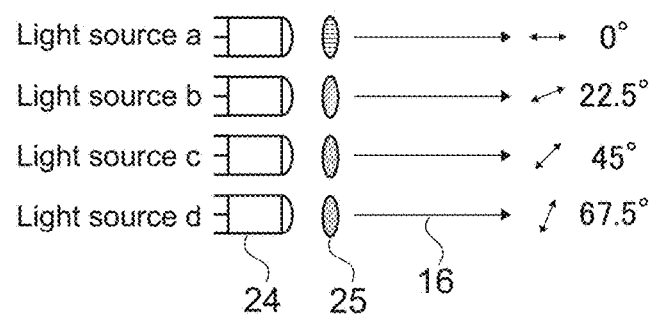

In FIG. 23D, a plurality of light sources 24, a plurality of lighting polarizers 25 set on the respective light sources 24, and a plurality of polarization light retaining fibers 16 that guides polarization light beams emitted from the plurality of lighting polarizers 25 are used. Thus, even with an endoscopic device having a thin distal end or the like, it is possible to switch the respective polarization light beams 3 at high speed.

Figure 24:
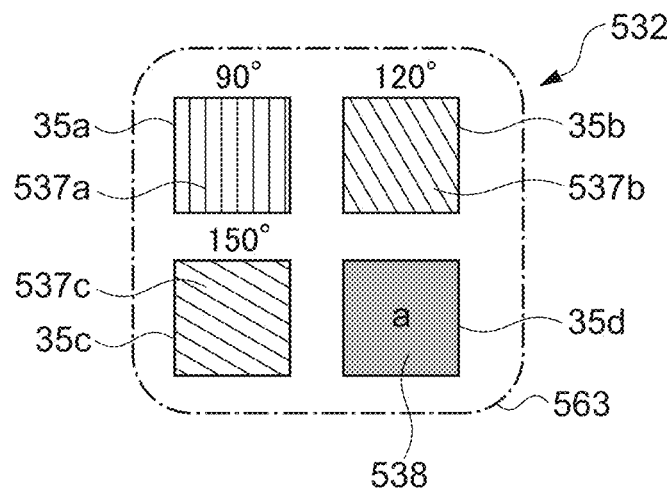
FIG. 24 A schematic view showing a configuration example of a polarization camera according to another embodiment.

FIG. 24 is a schematic view showing a configuration example of a polarization camera according to another embodiment. In a polarization camera 532 shown in FIG. 24, four pixels 35 are considered as a group and the three light-receiving polarizers 537 are provided in one group. FIG. 24 shows the four pixels 35a to 35d and light-receiving polarizers 537a to 537c arranged corresponding to the pixels 35a to 35c of them as a configuration example of the group. Therefore, with the polarization camera 532, a polarizer group 563 including three light-receiving polarizers 537a to 537c is provided in one group.

The light-receiving polarizer 537a having the polarization transmission axis 38 rotated by about 90° in the direction of left rotation from the reference direction 60 is arranged at the upper left of the polarizer group 563. The light-receiving polarizer 537b having the polarization transmission axis 38 rotated by about 120° in the direction of left rotation from the reference direction 60 is arranged at the upper right. The light-receiving polarizer 537c having the polarization transmission axis 38 rotated by about 150° in the direction of left rotation from the reference direction 60 is arranged at the lower left. Also with such a configuration, it is possible to obtain data points that enable the first intensity to be fitted.

It should be noted that an optical filter 538 is arranged at a lower right pixel 35d, for example. The RGB color filter is used as the optical filter 538, for example. With this configuration, it is possible to perform open nicol observation in visible light region. Moreover, a filter or the like that detects light outside a visible region, such as ultraviolet light and infrared light may be used as the optical filter 538 as appropriate. With this configuration, detection of a fluorescence marker and the like, infrared light observation, and the like are possible and it is possible to sufficiently assist biological tissue observation.

In the second embodiment, the rigid endoscope is used. Not limited thereto, the present technology is applicable also in a case where a soft endoscope or the like is used. For example, by using the lighting system and the like which have been described with reference to FIGS. 23A, 23B, 23C, and 23D as appropriate, it is possible to guide respective light beams while maintaining the polarization states even when the optical paths of polarization light beams and reflection light curves.

In the third embodiment, the first polarization camera 332a including the polarization sensors 39e to 39h with a pitch of 45° and the second polarization camera 332b including the polarization sensors 39i to 39l with a pitch of 45° are used. The configurations of the first and second polarization cameras 332a and 332b are not limited.

Figure 25:
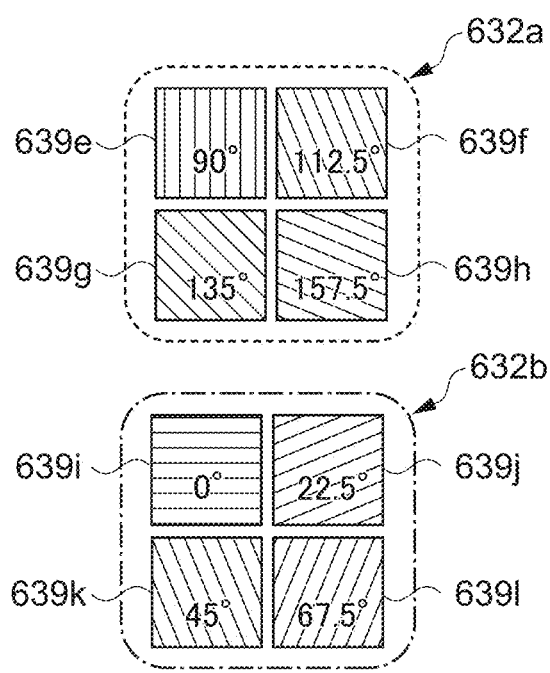
FIG. 25 A schematic view showing a configuration example of first and second polarization cameras according to another embodiment.

FIG. 25 is a schematic view showing a configuration example of first and second polarization cameras 632a and 632b according to another embodiment. As shown in FIG. 25, the first polarization camera 632a is provided with a polarization sensor 639e whose transmission angle φ is 90°, a polarization sensor 639f whose transmission angle φ is 112.5°, a polarization sensor 639g whose transmission angle φ is 135°, and a polarization sensor 639h whose transmission angle φ is 157.5°. Therefore, the first polarization camera 632a is constituted by four types of polarization sensors 639 with a pitch of 22.5°. It can also be said that it is a configuration similar to that of the polarization sensor 39c shown in FIG. 1.

In addition, the second polarization camera 632b is provided with a polarization sensor 639i whose transmission angle φ is 0°, a polarization sensor 639j whose transmission angle φ is 22.5°, a polarization sensor 639k whose transmission angle φ is 45°, and a polarization sensor 639l whose transmission angle φ is 67.5°. Therefore, the second polarization camera 632a is constituted by the four types of polarization sensors 639 with a pitch of 22.5° when the respective polarization sensors 639e to 639h of the first polarization camera 632a is rotated by 90°.

For example, it is assumed that the observation target 1 is observed by using the first and second polarization cameras 632a and 632b shown in FIG. 25. In this case, the polarization sensors 639e to 639h installed in the first polarization camera 632a is capable of performing crossed nicols observation four times. Therefore, it becomes easy to perform data obtaining and the like upon crossed nicols observation. Moreover, when performing open nicol observation, it is possible to obtain data whose transmission angle is smaller than 90° from the second polarization camera 632b and to obtain data whose transmission angle is equal to or larger than 90° from the first polarization camera 632. As a result, the imaging processing can be smoothly performed.

In addition, when a computer operated by the doctor or the like and another computer capable of communication via a network work in conjunction with each other, the observation method and the program according to the present technology are performed, and this makes it possible to configure the observation device according to the present technology.

That is, the observation method and the program according to the present technology can be performed not only in a computer system consisting of a single computer, but also in a computer system in which a plurality of computers cooperatively operates. It should be noted that in the present disclosure, the system means an aggregate of a plurality of components (devices, modules (parts), or the like) and it does not matter whether or not all the components are housed in a same casing. Therefore, a plurality of devices housed in separate casings and connected to one another via a network is treated as a system, and a single device including a plurality of modules housed in a single casing is also treated as a system.

The execution of the observation method and the program according to the present technology by the computer system include, for example, both of a case where calculation of biological tissue information and the like are performed by a single computer and a case where those processes are performed by different computers. Further, the execution of the respective processes by predetermined computers includes causing another computer to perform some or all of those processes and obtaining results thereof.

That is, the observation method and the program according to the present technology are also applicable to a cloud computing configuration in which one function is shared and cooperatively processed by a plurality of devices via a network.

In addition, the present technology is applicable to observation devices and observation systems not only in medical/biological fields but also in various kinds of other fields.

At least two feature parts of the feature parts according to the present technology described above can be combined. That is, the various feature parts described in the embodiments may be arbitrarily combined irrespective of the embodiments. Further, various effects described above are merely examples and are not limited, and other effects may be exerted.

At least two feature parts of the feature parts according to the present technology described above can be combined. That is, the various feature parts described in the embodiments may be arbitrarily combined irrespective of the embodiments. Further, various effects described above are merely examples and are not limited, and other effects may be exerted.

It should be noted that the present technology may also be configured as below.

(1) An observation device including:
an emission unit that sequentially emits a plurality of polarization light beams of mutually different polarization directions to a biological tissue;
an imaging unit including a plurality of pixels capable of outputting pixel signals respectively;
a polarization control unit that considers a predetermined number of pixels of the plurality of pixels as one group and causes mutually different polarization components of reflection light beams reflected by the biological tissue to be respectively incident upon respective ones of the predetermined number of pixels included in the one group; and
a calculation unit that calculates biological tissue information regarding the biological tissue on the basis of the pixel signals output from the respective ones of the predetermined number of pixels.

(2) The observation device according to (1), in which
the mutually different polarization components are polarization components corresponding to the respective polarization directions of the plurality of polarization light beams sequentially emitted.

(3) The observation device according to (1) or (2), in which
the emission unit sequentially emits the plurality of polarization light beams such that emission periods of the plurality of polarization light beams do not overlap each other.

(4) The observation device according to (3), in which
the calculation unit extracts, from the pixel signals output from the respective ones of the plurality of pixels, the pixel signal of a pixel upon which a polarization component corresponding to a polarization direction of a polarization light beam emitted during an emission period is incident and calculates the biological tissue information on the basis of the extracted pixel signal.

(5) The observation device according to any one of (1) to (4), in which
the emission unit sequentially emits the plurality of polarization light beams whose respective polarization directions are included in an angle range between a reference direction and an orthogonal direction orthogonal to the reference direction.

(6) The observation device according to any one of (1) to (5), in which
the polarization control unit includes a plurality of polarization elements, the plurality of polarization elements being arranged corresponding to the predetermined number of pixels in each group and each having a polarization axis corresponding to each of the respective polarization directions of the plurality of polarization light beams.

(7) The observation device according to (6), in which
the plurality of polarization elements each has the polarization axis that intersects with a polarization direction of a corresponding polarization light beam of the plurality of polarization light beams at a predetermined angle of intersection.

(8) The observation device according to (7), in which
the predetermined angle of intersection is 90°±2°.

(9) The observation device according to any one of (6) to (8), in which
the imaging unit includes an image sensor including the plurality of pixels,
the predetermined number of pixels is a pixel group including four pixels provided in the image sensor with two of the four pixels arranged in each of two directions orthogonal to each other, and
the plurality of polarization elements is a polarization element group including four or less polarization elements arranged corresponding to the pixel group.

(10) The observation device according to (9), in which
the polarization element group includes
a polarization element having a polarization axis rotated by about 90° in a predetermined direction from a reference direction,
a polarization element having a polarization axis rotated by about 112.5° in the predetermined direction from the reference direction,
a polarization element having a polarization axis rotated by about 135° in the predetermined direction from the reference direction, and
a polarization element having a polarization axis rotated by about 157.5° in the predetermined direction from the reference direction.

(11) The observation device according to (9), in which
the polarization element group includes
a polarization element having a polarization axis rotated by about 90° in a predetermined direction from a reference direction,
a polarization element having a polarization axis rotated by about 120° in the predetermined direction from the reference direction, and
a polarization element having a polarization axis rotated by about 1500 in the predetermined direction from the reference direction.

(12) The observation device according to any one of (1) to (11), in which
the emission unit includes
a plurality of light sources and
a plurality of polarization sections that respectively generates plurality of polarization light beams of the mutually different polarization directions from respective emission light beams of the plurality of light sources.

(13) The observation device according to any one of (1) to (12), in which
the emission unit includes
a light source and
a polarization section capable of rotating a polarization direction of a polarization light beam generated from an emission light beam of the light source.

(14) The observation device according to any one of (1) to (13), in which
the imaging unit includes
a first image sensor including a plurality of first pixels and
a second image sensor including a plurality of second pixels, further including:
a separation optical system that separates a reflection light beam from the biological tissue into a first separated light beam and a second separated light beam that travel in mutually different directions, causes the first separated light beam to be incident upon the first image sensor, and causes the second separated light beam to be incident upon the second image sensor.

(15) The observation device according to (14), in which
the polarization control unit includes
a plurality of first polarization elements that is arranged corresponding to the predetermined number of the first pixels, the predetermined number of the first pixels being considered as a first group, and
a plurality of second polarization elements that is arranged corresponding to the predetermined number of the second pixels, the predetermined number of the second pixels being considered as a second group.

(16) The observation device according to (15), in which
the emission unit is capable of emitting a non-polarization light beam to the biological tissue and
the calculation unit obtains a plurality of pixel signals output from the first pixels and the second pixels included in the first group and the second group in a case where the non-polarization light beam is emitted.

(17) The observation device according to (15) or (16), in which
the plurality of first polarization elements includes
a polarization element having a polarization axis substantially parallel to a reference direction,
a polarization element having a polarization axis rotated by about 45° in the predetermined direction from the reference direction,
a polarization element having a polarization axis rotated by about 90° in the predetermined direction from the reference direction, and
a polarization element having a polarization axis rotated by about 135° in the predetermined direction from the reference direction, and
the plurality of second polarization elements includes
a polarization element having a polarization axis rotated by about 22.5° in the predetermined direction from the reference direction,
a polarization element having a polarization axis rotated by about 67.5° in the predetermined direction from the reference direction,
a polarization element having a polarization axis rotated by about 112.5° in the predetermined direction from the reference direction, and
a polarization element having a polarization axis rotated by about 157.5° in the predetermined direction from the reference direction.

(18) The observation device according to (14), in which
the second image sensor is capable of detecting the second separated light beam while maintaining a polarization state of the second separated light beam.

(19) The observation device according to any one of (1) to (18), which is configured as an endoscope or a microscope.

(20) An observation method to be performed by a computer system, the method including:
sequentially emitting a plurality of polarization light beams of mutually different polarization directions to a biological tissue;
obtaining, for each group including a predetermined number of pixels of a plurality of pixels, pixel signals output from the respective ones of the predetermined number of pixels upon which mutually different polarization components of reflection light beams reflected by the biological tissue, are respectively incident; and
calculating biological tissue information regarding the biological tissue on the basis of the obtained pixel signals.

REFERENCE SIGNS LIST 1 observation target
3, 3a to 3d polarization light beam
4, 4a, 4b reflection light beam
5 polarization component
7 non-polarization light beam
20 lighting system
25, 25a to 25d, 225a to 225d, 325a to 325d lighting polarizer
33, 333a, 333b image sensor
34, 334a, 334b polarization unit
35, 35a to 35l pixel
37, 37a to 37l, 537a to 537d light-receiving polarizer
38 polarization transmission axis
42 image processing unit
43 analysis unit
51 anisotropic object
60 reference direction
61 direction of rotation
100, 300, 400 microscope device
200 endoscopic device

The invention claimed is:
1. An observation device, comprising:
a lighting device configured to sequentially emit a plurality of polarization light beams to a biological tissue, wherein
each of the plurality of polarization light beams has a specific polarization direction, and
the specific polarization direction of each of the plurality of polarization light beams is different;
an imaging unit including a plurality of pixels, wherein each of the plurality of pixels is configured to output a corresponding pixel signal of a plurality of pixel signals;
a plurality of polarization elements configured to control mutually different polarization components of reflection light beams reflected by the biological tissue to be incident upon respective pixels in a specific number of pixels of the plurality of pixels, wherein
the specific number of pixels includes one group of the plurality of pixels,
each of the plurality of polarization elements has a specific polarization transmission axis and corresponds to a pixel of the specific number of pixels,
the specific polarization transmission axis of each of the plurality of polarization elements is different, and
the specific polarization transmission axis of each of the plurality of polarization elements intersects the specific polarization direction of a corresponding polarization light beam of the plurality of polarization light beams at a specific angle of intersection; and a central processing unit (CPU) configured to calculate biological tissue information associated with the biological tissue based on the plurality of pixel signals outputted from the specific number of pixels of the plurality of pixels.

2. The observation device according to claim 1, wherein each of the mutually different polarization components is a polarization component that corresponds to the specific polarization direction of a corresponding polarization light beam of the plurality of polarization light beams sequentially emitted.

3. The observation device according to claim 2, wherein the CPU is further configured to:
extract, from the plurality of pixel signals, a pixel signal associated with a pixel upon which a polarization component corresponding to the specific polarization direction of a polarization light beam emitted during an emission period is incident; and
calculate the biological tissue information based on the extracted pixel signal.

4. The observation device according to claim 1, wherein the lighting device is further configured to sequentially emit the plurality of polarization light beams such that emission periods of the plurality of polarization light beams do not overlap.

5. The observation device according to claim 1, wherein the lighting device is further configured to sequentially emit each of the plurality of polarization light beams in the specific polarization direction, wherein
the specific polarization direction of each of the plurality of polarization light beams is in an angle range between a reference direction and an orthogonal direction, and
the orthogonal direction is orthogonal to the reference direction.

6. The observation device according to claim 1, wherein the specific angle of intersection is 90°±2°.

7. The observation device according to claim 1, wherein the imaging unit includes an image sensor,
the image sensor includes the plurality of pixels,
the specific number of pixels is a pixel group including four pixels in the image sensor,
two of the four pixels are in each of two directions orthogonal to each other, and
the plurality of polarization elements is a polarization element group including four or less polarization elements corresponding to the pixel group.

8. The observation device according to claim 7, wherein the polarization element group includes:
a first polarization element having the specific polarization transmission axis rotatable by about 90° in a specific direction from a reference direction,
a second polarization element having the specific polarization transmission axis rotatable by about 112.5° in the specific direction from the reference direction,
a third polarization element having the specific polarization transmission axis rotatable by about 135° in the specific direction from the reference direction, and
a fourth polarization element having the specific polarization transmission axis rotatable by about 157.5° in the specific direction from the reference direction.

9. The observation device according to claim 7, wherein the polarization element group includes:
a first polarization element having the specific polarization transmission axis rotatable by about 90° in a specific direction from a reference direction, a second polarization element having the specific polarization transmission axis rotatable by about 120° in the specific direction from the reference direction, and
a third polarization element having the specific polarization transmission axis rotatable by about 150° in the specific direction from the reference direction.

10. The observation device according to claim 1, further comprising:
a plurality of light sources configured to emit light beams, wherein
the lighting device that includes a plurality of polarization sections configured to generate each of the plurality of polarization light beams in the specific polarization direction from respective emission light beams of the plurality of light sources.

11. The observation device according to claim 1, further comprising:
a light source configured to emit light beam, wherein
the lighting device that includes a polarization section configured to rotate the specific polarization direction of a polarization light beam generated from the emitted light beam of the light source.

12. The observation device according to claim 1, wherein the imaging unit includes:
a first image sensor including a plurality of first pixels;
a second image sensor including a plurality of second pixels; and
a separation optical system configured to:
separate the reflection light beams from the biological tissue into a first separated light beam and a second separated light beam, wherein each of the first separated light beam and the second separated light beam travel in different directions;
cause the first separated light beam to be incident upon the first image sensor; and
cause the second separated light beam to be incident upon the second image sensor.

13. The observation device according to claim 12, wherein the plurality of polarization elements includes:
a plurality of first polarization elements corresponding to a specific number of the plurality of first pixels, wherein the specific number of the plurality of first pixels is a first group, and
a plurality of second polarization elements corresponding to a specific number of the plurality of second pixels, wherein the specific number of the plurality of second pixels is a second group.

14. The observation device according to claim 13, further comprising:
a light source configured to emit a non-polarization light beam to the biological tissue; and
the CPU further configured to obtain the plurality of pixel signals that is output from each of the plurality of first pixels in the first group and the plurality of second pixels in the second group in a case where the non-polarization light beam is emitted.

15. The observation device according to claim 13, wherein the plurality of first polarization elements includes:
a first polarization element having the specific polarization transmission axis substantially parallel to a reference direction;
a second polarization element having the specific polarization transmission axis rotatable by about 45° in a specific direction from the reference direction;
a third polarization element having the specific polarization transmission axis rotatable by about 90° in the specific direction from the reference direction; and
a fourth polarization element having the specific polarization transmission axis rotatable by about 135° in the specific direction from the reference direction, and
the plurality of second polarization elements includes:
a fifth polarization element having the specific polarization transmission axis rotatable by about 22.5° in the specific direction from the reference direction;
a sixth polarization element having the specific polarization transmission axis rotatable by about 67.5° in the specific direction from the reference direction;
a seventh polarization element having the specific polarization transmission axis rotatable by about 112.5° in the specific direction from the reference direction; and
an eighth polarization element having the specific polarization transmission axis rotatable by about 157.5° in the specific direction from the reference direction.

16. The observation device according to claim 12, wherein the second image sensor is configured to detect the second separated light beam while a polarization state of the second separated light beam is maintained.

17. The observation device according to claim 1, configured as an endoscope or a microscope.

18. An observation method, comprising:
in an observation device:
sequentially emitting, by a lighting device, a plurality of polarization light beams to a biological tissue, wherein
each of the plurality of polarization light beams has a specific polarization direction, and
the specific polarization direction of each of the plurality of polarization light beams is different;
outputting, by a plurality of pixels, a corresponding pixel signal of a plurality of pixel signals;
controlling, by a plurality of polarization elements, mutually different polarization components of reflection light beams reflected by the biological tissue to be incident upon respective pixels in a specific number of pixels of the plurality of pixels, wherein
the specific number of pixels includes one group of the plurality of pixels,
each of the plurality of polarization elements has a specific polarization transmission axis and corresponds to a pixel of the specific number of pixels,
the specific polarization transmission axis of each of the plurality of polarization elements is different, and
the specific polarization transmission axis of each of the plurality of polarization elements intersects the specific polarization direction of a corresponding polarization light beam of the plurality of polarization light beams at a specific angle of intersection; and
calculating, by a central processing unit (CPU), biological tissue information associated with the biological tissue based on the plurality of pixel signals outputted from the specific number of pixels of the plurality of pixels.

* * * * *